(12) United States Patent
Miyama et al.

(10) Patent No.: US 11,529,267 B2
(45) Date of Patent: Dec. 20, 2022

(54) NON-WOVEN FABRIC FOR LIQUID-PERMEABLE SHEET OF ABSORBENT ARTICLE, AND ABSORBENT ARTICLE WHICH INCLUDES SAID NON-WOVEN FABRIC AS LIQUID-PERMEABLE SHEET

(71) Applicant: UNICHARM CORPORATION, Ehime (JP)

(72) Inventors: Takuya Miyama, Kagawa (JP); Satoru Sakaguchi, Kagawa (JP); Masashi Uda, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 1185 days.

(21) Appl. No.: 16/067,083

(22) PCT Filed: Oct. 17, 2016

(86) PCT No.: PCT/JP2016/080735
§ 371 (c)(1),
(2) Date: Jun. 28, 2018

(87) PCT Pub. No.: WO2017/115528
PCT Pub. Date: Jul. 6, 2017

(65) Prior Publication Data
US 2020/0268571 A1 Aug. 27, 2020

(30) Foreign Application Priority Data
Dec. 28, 2015 (JP) .............................. JP2015-257464

(51) Int. Cl.
*A61F 13/15* (2006.01)
*A61F 13/511* (2006.01)
(Continued)

(52) U.S. Cl.
CPC ....... *A61F 13/51121* (2013.01); *D04H 1/425* (2013.01); *D04H 1/4291* (2013.01);
(Continued)

(58) Field of Classification Search
CPC ...... A61F 13/51121; A61F 2013/51007; A61F 2013/51019; A61F 2013/51038;
(Continued)

(56) References Cited

U.S. PATENT DOCUMENTS 6,025,050 A * 2/2000 Srinivasan .............. B32B 5/022
442/409
2001/0053899 A1 12/2001 Mizutani et al.
(Continued)

FOREIGN PATENT DOCUMENTS

JP H9-505218 A 5/1997
JP 2002-651 A 1/2002
(Continued)

OTHER PUBLICATIONS

International Search Report for PCT/JP2016/080735, filed on Oct. 17, 2016, 2pp.

*Primary Examiner* — Jacqueline F Stephens
(74) *Attorney, Agent, or Firm* — Hauptman Ham, LLP

(57) ABSTRACT

This non-woven fabric comprises the following configuration. In this non-woven fabric for a liquid-permeable sheet of an absorbent article, said non-woven fabric comprising a thickness direction, a planar direction, a first face, and a second face: the non-woven fabric includes thermoplastic resin fibers, and cellulosic fibers, at least a portion whereof configures a plurality of fiber masses; the non-woven fabric further comprises a plurality of spaces which are adjacent to first regions of each of the plurality of fiber masses, said first regions facing the first face; and each of the plurality of fiber masses is not bonded to the thermoplastic resin fibers.

14 Claims, 9 Drawing Sheets

(51) Int. Cl.
*D04H 1/425* (2012.01)
*D04H 1/4291* (2012.01)
*D04H 1/435* (2012.01)
*A61F 13/51* (2006.01)

(52) U.S. Cl.
CPC .... *D04H 1/435* (2013.01); *A61F 2013/51007* (2013.01); *A61F 2013/51019* (2013.01); *A61F 2013/51026* (2013.01); *A61F 2013/51038* (2013.01); *D10B 2509/026* (2013.01)

(58) Field of Classification Search
CPC ...... D04H 1/425; D04H 1/4291; D04H 1/435; D10B 2509/026
See application file for complete search history.

(56) References Cited

U.S. PATENT DOCUMENTS

| | | | |
|---|---|---|---|
| 2002/0064624 | A1 | 5/2002 | Mizutani et al. |
| 2015/0314560 | A1* | 11/2015 | Kauschke ......... A61F 13/15203 428/172 |
| 2018/0140479 | A1 | 5/2018 | Uda et al. |

FOREIGN PATENT DOCUMENTS

| | | | |
|---|---|---|---|
| JP | 2002-159531 | A | 6/2002 |
| JP | 5829326 | B1 | 12/2015 |
| JP | 5829327 | B1 | 12/2015 |
| JP | 5829349 | B1 | 12/2015 |
| WO | 95/13776 | A1 | 5/1995 |
| WO | 2015/167815 | A1 | 11/2015 |

\* cited by examiner

NON-WOVEN FABRIC FOR
LIQUID-PERMEABLE SHEET OF
ABSORBENT ARTICLE, AND ABSORBENT
ARTICLE WHICH INCLUDES SAID
NON-WOVEN FABRIC AS
LIQUID-PERMEABLE SHEET

RELATED APPLICATIONS

The present application is a National Phase of International Application Number PCT/JP2016/080735, filed Oct. 17, 2016 and claims priority to Japanese Application No. 2015-257464, filed on Dec. 28, 2015.

FIELD

The present disclosure relates to a nonwoven fabric to be used for a liquid permeable sheet of an absorbent article, and an absorbent article which includes the nonwoven fabric as the liquid permeable sheet.

BACKGROUND

In an absorbent article such as a disposable diaper, and a sanitary napkin, etc., in order to obtain feeling of security, etc., by natural materials, a nonwoven fabric which includes cotton that is natural fibers as a material of a liquid permeable sheet, etc., has been considered.

As such a nonwoven fabric, for example, in Patent Document 1, a surface layer and an absorbent article which includes the surface layer are described, wherein the surface layer includes hydrophobic fibers and hydrophilic fibers which are shorter than the hydrophobic fibers, and further, the hydrophobic fibers are heat fused with each other, at least a portion of the hydrophilic fibers are distributed in an assembled state in the sheet, and at least a portion of the hydrophilic fibers of the assemblies is fused to the surface of the hydrophobic fibers.

PRIOR ART DOCUMENTS

Patent Documents

[Patent Document 1] Japanese Unexamined Patent Publication No. 2002-651

DISCLOSURE OF THE INVENTION

Problems to be Solved by the Invention

The objects of the absorbent article described in Patent Document 1 are to make it easier for large amount of liquid to permeate the absorbent layer, while making it easier for small amount of liquid to be retained within the surface layer, to make it difficult to give moist feeling to the skin of the wearer, and to provide an absorbent article with pleasant wearing feeling, and thus the invention described in Patent Document 1 is made from the viewpoint mainly of the retention of liquid.

The object of the present disclosure is to provide a nonwoven fabric to be used for a liquid permeable sheet of an absorbent article, which makes it difficult for moisture and liquid from the absorbent body to permeate the space between the absorbent article and the wearer both under a non-pressured state and under a pressured state, and makes it difficult for the wearer to sense steaming feeling and rewetting feeing.

Means for Solving the Problems

The inventors of the present disclosure found out that a nonwoven fabric to be used for a liquid permeable sheet of an absorbent article, which includes a thickness direction, a plane direction, a first surface, and a second surface, the nonwoven fabric comprising: thermoplastic resin fibers; cellulose based fibers a portion of which configuring a plurality of fiber masses; and a plurality of gap portions which are adjacent to a first region that faces the first surface in each of the plurality of fiber masses, wherein each of the plurality of fiber masses is not joined to the thermoplastic resin fibers is the solution to the problem.

Effects of the Invention

The nonwoven fabric to be used for a liquid permeable sheet of an absorbent article according to the present disclosure makes it difficult for moisture and liquid from the absorbent body to permeate the space between the absorbent article and the wearer both under a non-pressured state and under a pressured state, and makes it difficult for the wearer to sense steaming feeling and rewetting feeing.

MODE FOR CARRYING OUT THE INVENTION

Definitions

Figure 1:
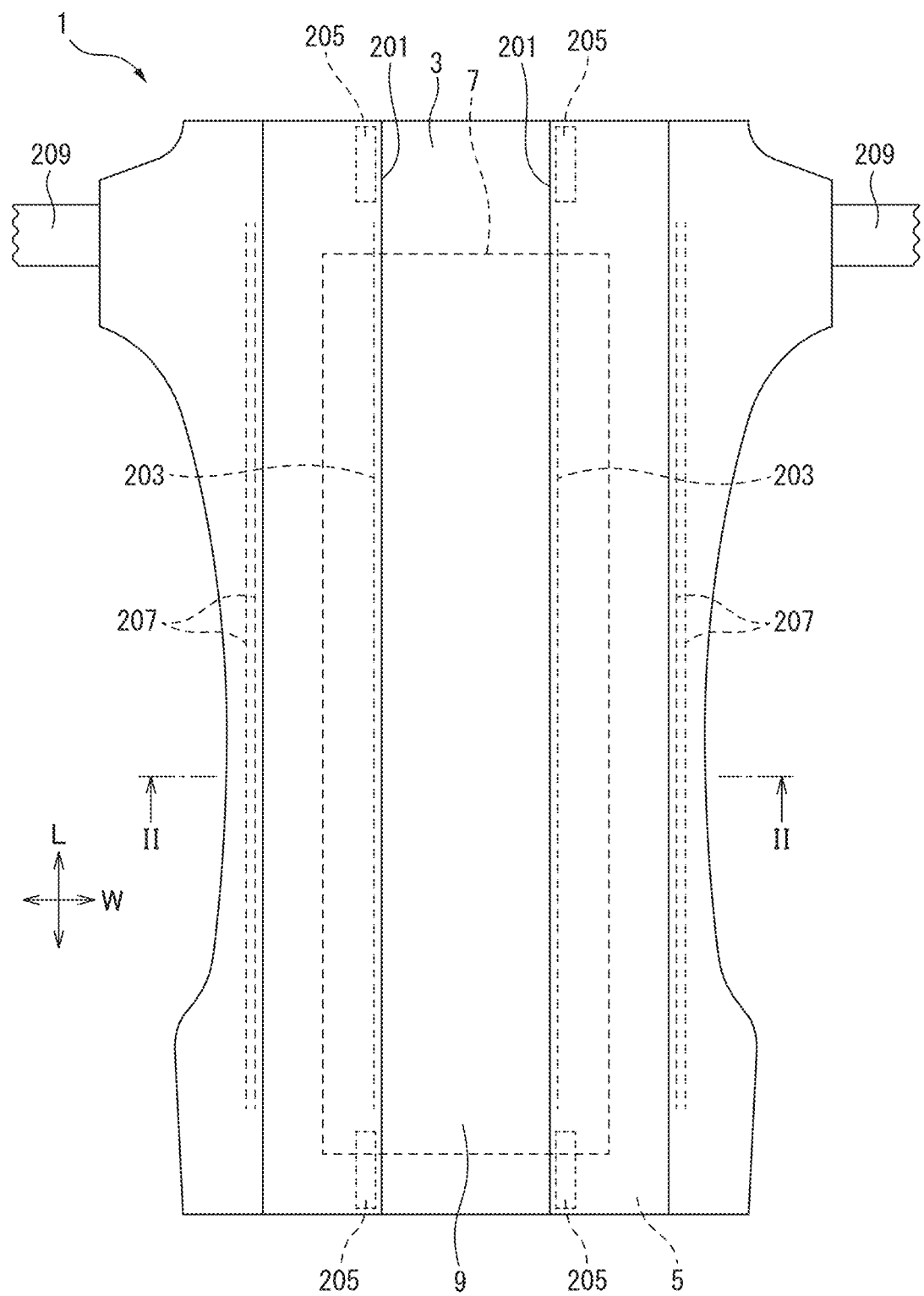
FIG. 1 is an expanded view of the front side of an absorbent article 1 which includes the nonwoven fabric according to the first embodiment as a liquid permeable sheet 3.

"Joining" of a Fiber Mass and a Thermoplastic Resin Fiber

In the present description, the terms "joining" and "in a state of being joined" with regard to the fiber masses and the thermoplastic resin fibers mean "fused" and "in a state of being fused", respectively. Accordingly, the state in which "each of the plurality of fiber masses is not joined to the thermoplastic resin fibers" means that "each of the plurality of fiber masses is not fused to the thermoplastic resin fibers".

Consequently, entangling (in a state of being entangled) of the cellulose based fibers configuring the fiber masses and the thermoplastic resin fibers configuring a matrix and/or the cellulose based fibers is not included in the above described "joining (in a state of being joined)", and the nonwoven fabric of the present disclosure may include the entangling of the cellulose based fibers configuring the fiber masses and the thermoplastic resin fibers configuring a matrix and/or the cellulose based fibers.

Incidentally, as the above described entangling, a state in which the cellulose based fibers configuring the fiber masses enter into the matrix without fusing to thermoplastic resin fibers configuring the matrix and/or the cellulose based fibers, and a state in which the thermoplastic resin fibers configuring a matrix and/or the cellulose based fibers enter into the fiber masses without fusing to the cellulose based fibers configuring the fiber masses, etc., may be mentioned.

"Joining" of Thermoplastic Resin Fibers with Each Other

In the present description, the terms "joining" and "in a state of being joined" with regard to the thermoplastic resin fibers mean "fused" and "in a state of being fused", respectively, similarly to the case of the fiber masses and the thermoplastic resin fibers.

The present disclosure relates to the following aspects.
[Aspect 1] A nonwoven fabric to be used for a liquid permeable sheet of an absorbent article, which includes a thickness direction, a plane direction, a first surface, and a second surface, the nonwoven fabric comprising:
  thermoplastic resin fibers;
  cellulose based fibers a portion of which configuring a plurality of fiber masses; and
  a plurality of gap portions which are adjacent to a first region that faces the first surface in each of the plurality of fiber masses, wherein
  each of the plurality of fiber masses is not joined to the thermoplastic resin fibers.

Since the above described nonwoven fabric includes the fiber masses of the cellulose based fibers and the gap portions which are adjacent to the first region of the fiber masses, under a non-pressured state to which body pressure, etc., is not applied, the fiber masses absorb and retain intensively (spotwise) the moisture which has permeated the nonwoven fabric and is about to be discharged from the absorbent body to the space between the absorbent article and the wearer, through the gap portions, whereby in the plane direction of the nonwoven fabric, the area of the portions which retain the moisture can be made smaller (spotwise), and the amount of moisture which permeates the nonwoven fabric and is discharged from the absorbent body to the space between the absorbent article and the wearer can be reduced.

Further, even under a pressured state to which body pressure, etc., is applied, since the gap portions are preferentially compressed rather than the fiber masses, the fiber masses absorb and retain intensively (spotwise) the moisture which has permeated the nonwoven fabric and is about to be discharged from the absorbent body to the space between the absorbent article and the wearer, through the remaining gap portions, whereby in the plane direction of the nonwoven fabric, the area of the portions which retain the moisture can be made smaller (spotwise), and the amount of moisture which permeates the nonwoven fabric and is discharged from the absorbent body to the space between the absorbent article and the wearer can be reduced.

In the above described nonwoven fabric, under a non-pressured state, the fiber masses of the cellulose based fibers absorb and retain the liquid which permeates the nonwoven fabric and is about to be discharged from the absorbent body to the space between the absorbent article and the wearer. Since the above described fiber masses are not joined to the thermoplastic resin fibers and can move mainly in the thickness direction (toward the first surface) within the gap portions, it is difficult for the fiber masses to retain the state of being in contact with the thermoplastic resin fibers for a long period of time, and it is difficult for the liquid retained by the fiber masses to be transmitted to the thermoplastic resin fibers so as to return to the wearer's side.

Further, in the above described nonwoven fabric, under a pressured state, since the gap portions are preferentially compressed rather than the fiber masses, it is difficult for the fiber masses to be crushed, and for the liquid retained by the fiber masses to be pushed out from the fiber masses. Still further, since the fiber masses are not joined to the thermoplastic resin fibers, it is difficult for the liquid which has been pushed out from the fiber masses to be transmitted to the thermoplastic resin fibers so as to return to the wearer's side.

Accordingly, the above described nonwoven fabric makes it difficult for liquid from the absorbent body to permeate the space between the absorbent article and the wearer both under a non-pressured state and under a pressured state, and makes it difficult for the wearer to sense rewetting feeing.

[Aspect 2] The nonwoven fabric according to aspect 1, further comprising:
  a matrix which includes at least the thermoplastic resin fibers; and
  the plurality of fiber masses which are distributed in the matrix.

In the above described nonwoven fabric, the fiber masses which are distributed in the matrix including the thermoplastic resin fibers can effectively absorb and retain the moisture which has permeated the nonwoven fabric and is about to be discharged from the absorbent body to the space between the absorbent article and the wearer, through the gap portions by the entire nonwoven fabric, whereby the amount of moisture which permeates the nonwoven fabric and is discharged from the absorbent body to the space between the absorbent article and the wearer can be further reduced compared to the nonwoven fabric of aspect 1.

[Aspect 3] The nonwoven fabric according to aspect 1 or 2, wherein
  an outer edge in the plane direction of the gap portions is present on an outer side than an outer edge in the plane direction of the fiber masses.

In the above described nonwoven fabric, since the outer edge of the gap portions is present on the outer side than the outer edge of the fiber masses, and the fiber masses can absorb and retain the moisture which is about to be discharged from the absorbent body to the space between the absorbent article and the wearer, through the gap portions by the entire first region, the amount of moisture which permeates the nonwoven fabric and is discharged from the absorbent body to the space between the absorbent article and the wearer can be reduced. Accordingly, the above described nonwoven fabric makes it difficult for moisture which is gas from the absorbent body to permeate the space between the absorbent article and the wearer both under a non-pressured state and under a pressured state, and makes it difficult for the wearer to sense steaming feeing.

Further, in the above described nonwoven fabric, since the outer edge of the gap portions is present on the outer side than the outer edge of the fiber masses, it is easy for the fiber masses to move in the thickness direction (toward the first surface) within the gap portions, and it is difficult for the liquid retained by the fiber masses to be transmitted to the thermoplastic resin fibers so as to return to the wearer's side, both under a non-pressured state and under a pressured state. Accordingly, the above described nonwoven fabric makes it difficult for liquid from the absorbent body to permeate the space between the absorbent article and the wearer both under a non-pressured state and under a pressured state, and makes it difficult for the wearer to sense rewetting feeing.

[Aspect 4] The nonwoven fabric according to any one of aspects 1 to 3, further comprising a gap portion which is adjacent to a second region which faces the second surface in at least a portion of the plurality of fiber masses.

Since the above described nonwoven fabric further includes the gap portion which is adjacent to the second region which faces the second surface of at least a portion of the plurality of fiber masses, under a non-pressured state, the fiber masses can absorb and retain the moisture which is about to be discharged from the absorbent body to the space between the absorbent article and the wearer, through the gap portions from the first region and the second region, whereby the amount of moisture which permeates the nonwoven fabric and is discharged from the absorbent body to the space between the absorbent article and the wearer can be reduced. Further, in the above described nonwoven fabric, under a pressured state, although the gap portions which are adjacent to the first region and the second region of the fiber masses are preferentially compressed rather than the fiber masses, it is easy for the gap portions to retain the gaps. Accordingly, since the above described nonwoven fabric absorbs and retains the moisture which has permeated the nonwoven fabric and is about to be discharged from the absorbent body to the space between the absorbent article and the wearer, through the gap portions which are more easily remained, whereby the amount of moisture which permeates the nonwoven fabric and is discharged from the absorbent body to the space between the absorbent article and the wearer can be reduced.

Accordingly, the above described nonwoven fabric makes it difficult for moisture which is gas from the absorbent body to permeate the space between the absorbent article and the wearer both under a non-pressured state and under a pressured state, and makes it difficult for the wearer to sense steaming feeling.

Further, since the above described nonwoven fabric further includes the gap portion which is adjacent to the second region which faces the second surface of at least a portion of the plurality of fiber masses, it is easy for the fiber masses to move in the thickness direction (toward the first surface and the second surface) within the gap portions, and it is difficult for the liquid retained by the fiber masses to be transmitted to the thermoplastic resin fibers so as to return to the wearer's side, both under a non-pressured state and under a pressured state. Accordingly, the above described nonwoven fabric makes it difficult for liquid from the absorbent body to permeate the space between the absorbent article and the wearer both under a non-pressured state and under a pressured state, and makes it difficult for the wearer to sense rewetting feeing.

[Aspect 5] The nonwoven fabric according to any one of aspects 1 to 4, wherein
the thermoplastic resin fibers are joined to each other.

In the above described nonwoven fabric, since the thermoplastic resin fibers are joined to each other, it is easy for the gap portions which are formed between the thermoplastic resin fibers and the fiber masses of the cellulose based fibers to retain the shape thereof, and it is even easier to demonstrate the above described effects.

[Aspect 6] The nonwoven fabric according to any one of aspects 1 to 5, wherein
the nonwoven fabric includes the cellulose based fibers with a proportion of 3 to 35% by mass.

Since the above described nonwoven fabric includes the cellulose based fibers with the predetermined proportion, it is easier for the fiber masses of the cellulose based fibers to absorb and retain intensively (spotwise) the moisture which has permeated the nonwoven fabric and is about to be discharged from the absorbent body to the space between the absorbent article and the wearer, through the gap portions, whereby in the plane direction of the nonwoven fabric, the area of the portions which retain the moisture can be made smaller (spotwise), and the amount of moisture which permeates the nonwoven fabric and is discharged from the absorbent body to the space between the absorbent article and the wearer can be reduced.

[Aspect 7] The nonwoven fabric according to any one of aspects 1 to 6, wherein
the cellulose based fibers have a shorter average fiber length than the thermoplastic resin fibers.

In the above described nonwoven fabric, since the cellulose based fibers have a shorter fiber length than the thermoplastic resin fibers, it is easier for the fiber masses of the cellulose based fibers to be present in a state of being separated from the thermoplastic resin fibers within the nonwoven fabric, whereby it is even easier to demonstrate the above described effects.

[Aspect 8] The nonwoven fabric according to any one of aspects 1 to 7, wherein
the cellulose based fibers include organic cotton.

In the above described nonwoven fabric, since the cellulose based fibers include organic cotton, it is easier for the user to sense feeling of security. Further, in the above described nonwoven fabric, since the cellulose based fibers include organic cotton, it is easier for the cellulose based fibers to have a shorter fiber length than the thermoplastic resin fibers, whereby it is even easier for the above described nonwoven fabric to demonstrate the above described effects.

[Aspect 9] The nonwoven fabric according to any one of aspects 1 to 8, wherein
the cellulose based fibers include *Gossypium hirsutum* cotton.

In the above described nonwoven fabric, since the cellulose based fibers include *Gossypium hirsutum* cotton, it is easier for the user to sense feeling of security. Further, in the above described nonwoven fabric, since the cellulose based fibers include *Gossypium hirsutum* cotton, it is easier for the cellulose based fibers to have a shorter fiber length than the thermoplastic resin fibers, whereby it is even easier for the above described nonwoven fabric to demonstrate the above described effects.

[Aspect 10] The nonwoven fabric according to any one of aspects 1 to 9, wherein
the nonwoven fabric has a multiple-layer structure which includes a skin side layer having a skin contact surface, and
the nonwoven fabric includes the plurality of fiber masses in a layer other than the skin side layer.

In the above described nonwoven fabric, since the fiber masses are present in a layer other than the skin side layer of the nonwoven fabric, at the time when being used, it is difficult for the fiber masses of the cellulose based fibers to drop out of the nonwoven fabric. Further, in the above described nonwoven fabric, since the fiber masses are present in a layer other than the skin side layer of the nonwoven fabric, it is difficult for the liquid which is absorbed and retained by the fiber masses of the cellulose based fibers to come in contact with the skin of the wearer, and for the wearer to sense uncomfortable feeling.

[Aspect 11] The nonwoven fabric according to any one of aspects 1 to 10, wherein the nonwoven fabric further comprises:

a plurality of protruded portions which protrude in a direction from the first surface to the second surface, in the second surface; and a plurality of dented portions which are dented in a direction from the second surface to the first surface, in the first surface, wherein each of the plurality of protruded portions and each of the plurality of dented portions are overlapped with each other in the thickness direction.

Since the above described nonwoven fabric includes a plurality of dented portions which are dented in the second surface, in a case of being used as a liquid permeable sheet, separated regions are to be formed between the dented portions in the second surface and the absorbent body. Accordingly, when the liquid which is absorbed and retained by the absorbent body is released from the absorbent body as moisture by evaporation, etc., since the cellulose based fibers of the nonwoven fabric, and especially the fiber masses thereof absorb and retain the moisture, and further, the moisture state is kept in the gap portions adjacent to the fiber masses and in the above described separated regions (that is, the gap portions and the separated regions are in a high humidity state), a state like a gas-liquid equilibrium is to be established between the moisture (gas phase) within the separated regions and the liquid (liquid phase) retained by the absorbent body, whereby the moisture is suppressed from being released any further from the absorbent body. Accordingly, it is difficult for the wearer to sense steaming feeling.

[Aspect 12] The nonwoven fabric according to aspect 11, wherein each of the plurality of protruded portions configures a ridge portion which extends in one direction, and the nonwoven fabric further comprises a plurality of groove portions each of which being present between the adjacent ridge portions and including a groove bottom portion, wherein each of the plurality of groove portions includes, in the groove bottom portion, a plurality of recessed portions which are disposed intermittently in the one direction and are recessed in the direction from the first surface to the second surface, each of the plurality of recessed portions including a bottom portion.

The above described nonwoven fabric, when being used as a liquid permeable sheet, can form the separated regions between the liquid permeable sheet and the absorbent body. To be more specific, the above described nonwoven fabric, when being used as a liquid permeable sheet, can form the separated regions between the dented portions thereof and the absorbent body. Further, in the above described nonwoven fabric, even in the case in which the nonwoven fabric is temporarily crushed under a pressured state, and the separated regions are also temporarily crushed according therewith, it is easy to be recovered to the original shape, and for the separated regions to be restored. Accordingly, in the above described nonwoven fabric, it is even more difficult for the wearer to sense steaming feeling for a long period of time, compared to the nonwoven fabric of aspect 11.

[Aspect 13] An absorbent article which includes a liquid permeable sheet, a liquid impermeable sheet, and an absorbent body that is present between the liquid permeable sheet and the liquid impermeable sheet, wherein the liquid permeable sheet is the nonwoven fabric according to any one of aspects 1 to 12.

In the above described absorbent article, since the above described nonwoven fabric has the above described effects, the absorbent article makes it difficult for moisture and liquid from the absorbent body to permeate the space between the absorbent article and the wearer both under a non-pressured state and under a pressured state, and makes it difficult for the wearer to sense steaming feeling and rewetting feeing.

[Aspect 14] The absorbent article according to aspect 13, wherein the second surface of the nonwoven fabric configures a skin contact surface of the liquid permeable sheet.

In the above described absorbent article, since the second surface of the nonwoven fabric configures the skin contact surface of the liquid permeable sheet, the gap portions are to be disposed on the first surface side of the fiber masses, that is, the absorbent body side, whereby both under a non-pressured state and under a pressured state, the fiber masses can absorb and retain intensively (spotwise) the moisture which has permeated the nonwoven fabric and is about to be discharged from the absorbent body to the space between the absorbent article and the wearer, through the gap portions which are present on the absorbent body side, and thus the amount of moisture which permeates the nonwoven fabric and is discharged from the absorbent body to the space between the absorbent article and the wearer can be reduced.

[Aspect 15] The absorbent article according to aspect 13 or 14, wherein the liquid impermeable sheet has a moisture permeability.

In the above described absorbent article, since the liquid impermeable sheet has a moisture permeability, the moisture inside the absorbent article can be discharged through the liquid impermeable sheet, whereby the moisture inside the absorbent article and the moisture which is kept between the absorbent article and the wearer can be reduced. Accordingly, the above described absorbent article is excellent in steaming-free property.

Hereinbelow, the nonwoven fabric to be used for a liquid permeable sheet of an absorbent article according to the present disclosure is explained in detail, however, for the sake of explanation, the state in which the above described nonwoven fabric is used for the liquid permeable sheet of an absorbent article is explained.

Figure 2:
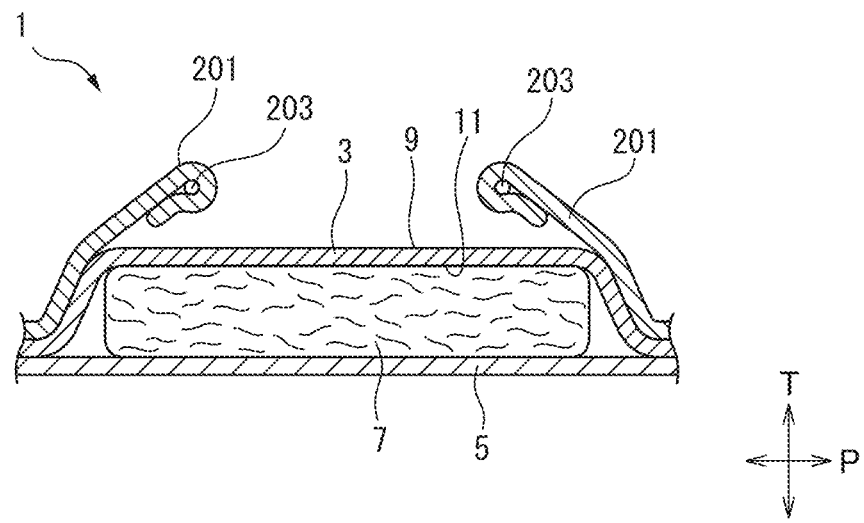
FIG. 2 is a partial end view along II-II end surface of FIG. 1.
Figure 3:
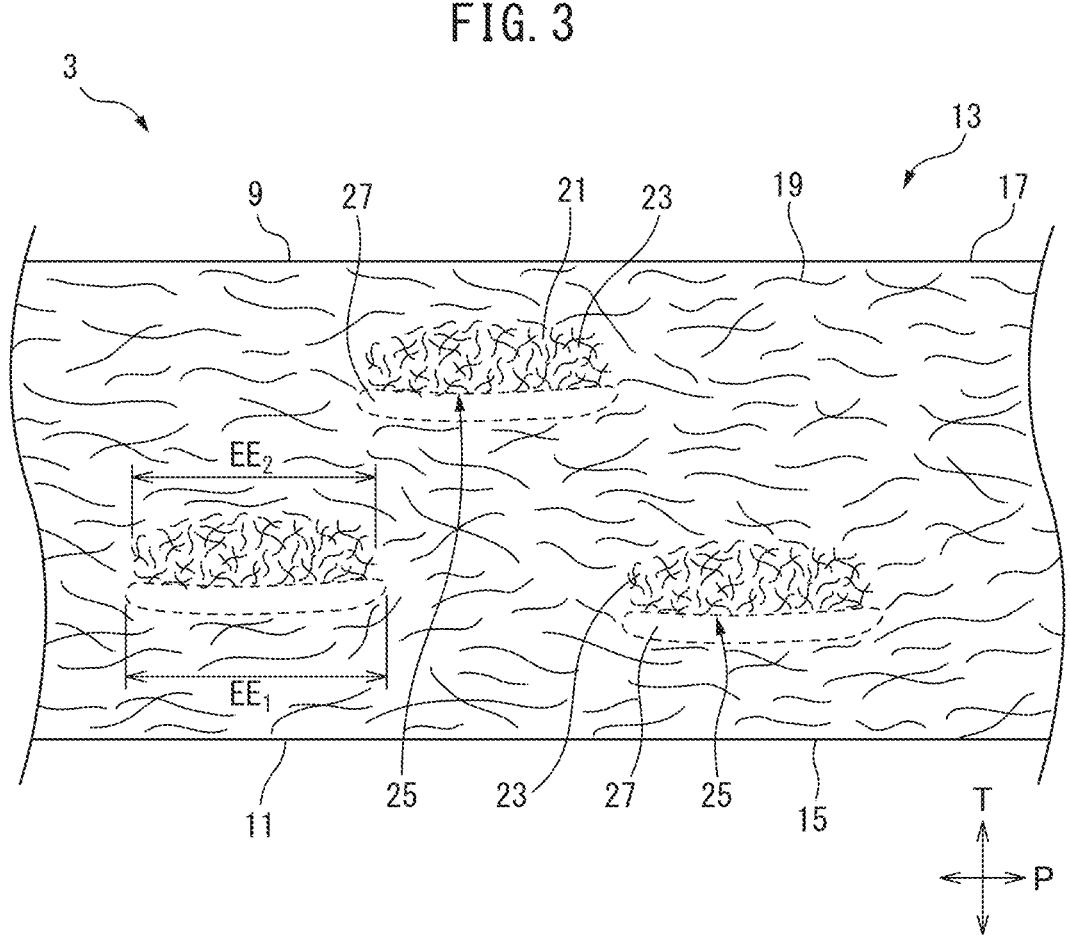
FIG. 3 is a partial enlarged view of the liquid permeable sheet 3 of FIG. 2.

FIG. 1 is an expanded view of the front side of the absorbent article 1 and to be more specific, a tape type disposable diaper, which includes the nonwoven fabric according to one embodiment of the present disclosure (the first embodiment) as the liquid permeable sheet 3. FIG. 2 is a partial end view along II-II end surface of FIG. 1. FIG. 3 is a partial enlarged view of the vicinity of the liquid permeable sheet 3 of FIG. 2. Incidentally, FIG. 3 is a view for schematically explaining the relationship between the thermoplastic resin fibers 19, the fiber masses 23 of the cellulose based fibers 21, and gap portions 27, etc. in the liquid permeable sheet 3 (the nonwoven fabric 13), however is not intended for the present disclosure to be interpreted in a limited manner.

In the first embodiment, the absorbent article 1 includes the liquid permeable sheet 3, the liquid impermeable sheet 5, and the absorbent body 7 which is present between the liquid permeable sheet 3 and the liquid impermeable sheet 5. The absorbent article 1 includes the longitudinal direction L and the width direction W.

Incidentally, in the first embodiment, as shown in FIG. 1, the absorbent article 1 further includes the pair of leakage barriers 201 which include the elastic members 203, the fixed portions 205 so as to fix the leakage barriers 201 to the liquid permeable sheet 3, the elastic members 207, the tape fasteners 209, etc., however, since these members are known in the technical field, the explanation thereof is omitted.

In the first embodiment, the liquid permeable sheet 3 includes the skin contact surface 9 which is to come in contact with the skin of the wearer, and the clothing side surface 11 which is the surface on the opposite side of the skin contact surface 9 and is disposed on the further clothing side of the wearer than the skin contact surface 9.

As shown in FIG. 3, the nonwoven fabric 13 which configures the liquid permeable sheet 3 includes the thickness direction T and the plane direction P, and further includes the first surface 15 and the second surface 17, the first surface 15 forms the clothing side surface 11 of the liquid permeable sheet 3, and the second surface 17 forms the skin contact surface 9 of the liquid permeable sheet 3.

The nonwoven fabric 13 includes the thermoplastic resin fibers 19 and the cellulose based fibers 21, the cellulose based fibers 21 form the plurality of fiber masses 23, and the plurality of fiber masses 23 are disposed in the matrix of the thermoplastic resin fibers 19 with a space apart, in other words, the plurality of fiber masses 23 are distributed in the matrix of the thermoplastic resin fibers 19.

The nonwoven fabric 13 further includes the plurality of gap portions 27 which are adjacent to the first region 25 that faces the first surface 15 of each of the plurality of fiber masses 23.

The fiber masses 23, and to be more specific, the cellulose based fibers 21 configuring the fiber masses 23, are not joined to the thermoplastic resin fibers 19 configuring the matrix.

As shown in FIG. 3, in the nonwoven fabric 13, the outer edge $EE_1$ in the plane direction P of the gap portions 27 is present on an outer side than the $EE_2$ in the plane direction P of the fiber masses 23. Accordingly, since the fiber masses 23 can absorb and retain the moisture which is about to be discharged from the absorbent body 7 to the inner side of the absorbent article 1 by the entire first region 25 through the gap portions 27, the amount of moisture which permeates the liquid permeable sheet 3 (the nonwoven fabric 13) and is discharged from the absorbent body 7 to the inner side of the absorbent article 1 can be reduced. Consequently, the liquid permeable sheet 3 (the nonwoven fabric 13) makes it difficult for moisture which is gas from the absorbent body 7 to permeate the inner side of the absorbent article 1 through the liquid permeable sheet 3 both under a non-pressured state and under a pressured state, and makes it difficult for the wearer to sense steaming feeing.

Further, in the liquid permeable sheet 3 (the nonwoven fabric 13), since the outer edge $EE_1$ of the gap portions 27 is present on the outer side than the outer edge $EE_2$ of the fiber masses 23, it is easy for the fiber masses 23 to move in the thickness direction T (toward the first surface) within the gap portions 27, and it is difficult for the liquid retained by the fiber masses 23 to be transmitted to the thermoplastic resin fibers 19 so as to return to the wearer's side, both under a non-pressured state and under a pressured state. Accordingly, the liquid permeable sheet 3 (the nonwoven fabric 13) makes it difficult for liquid to permeate therethrough from the absorbent body 7 side to the wear's side both under a non-pressured state and under a pressured state, and makes it difficult for the wearer to sense rewetting feeing.

In the first embodiment, the liquid impermeable sheet 5 has a moisture permeability. Accordingly, the moisture inside the absorbent article 1 can be discharged through the liquid impermeable sheet 5, whereby the moisture inside the absorbent article 1 and the moisture which is kept between the absorbent article 1 and the wearer can be reduced.

Figure 4:
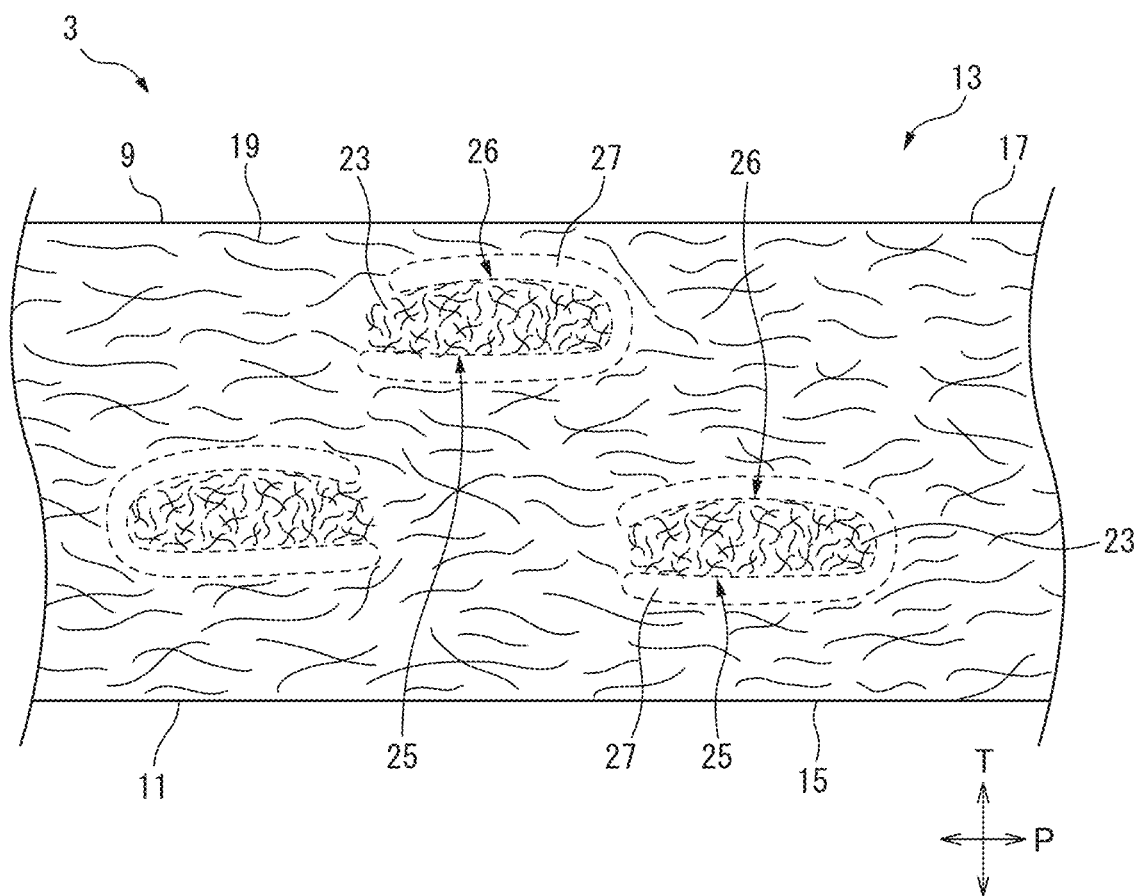
FIG. 4 is a view for explaining a nonwoven fabric 13 according to another embodiment (a second embodiment) of the present disclosure.

FIG. 4 is a view for explaining the nonwoven fabric 13 according to another embodiment (the second embodiment) of the present disclosure, and is an end view which corresponds to FIG. 3. Incidentally, similarly to FIG. 3, FIG. 4 is also a view for schematically explaining the relationship between the thermoplastic resin fibers 19, the fiber masses 23 of the cellulose based fibers 21, and gap portions 27, etc., however is not intended for the present disclosure to be interpreted in a limited manner.

The nonwoven fabric 13 according to the second embodiment further includes the gap portion 27 which is adjacent to the second region 26 which faces the second surface 17 of the nonwoven fabric 13 of each of the plurality of fiber masses 23. To be more specific, in each of the fiber masses 23, the gap portion 27 adjacent to the first region 25 and the gap portion 27 adjacent to the second region 26 are connected to each other. Since the other configurations are the same as those of the nonwoven fabric according to the first embodiment, the explanation thereof is omitted.

In the first embodiment and the second embodiment, the nonwoven fabric 13 has a single-layer structure, however, the nonwoven fabric of the present disclosure may have a multiple-layer structure, for example, a two-layer structure of a skin side layer which has a skin contact surface and a clothing side layer which is disposed on the further clothing side than the skin side layer, or a three-layer structure of a skin side layer which has a skin contact surface, a clothing side layer which is disposed on the clothing side and a middle layer which is present between the skin side layer and the clothing side layer. As such a nonwoven fabric, the one in which the nonwoven fabric itself has a multiple-layer structure, and the one in which the web before forming the nonwoven fabric has a multiple-layer structure, etc., may be mentioned.

In such an embodiment, preferably, the fiber masses of the cellulose based fibers are not included in the skin side layer and are included in a layer other than the skin side layer. To be more specific, in a case in which the nonwoven fabric of the present disclosure has a two-layer structure of a skin side layer and a clothing side layer, preferably, the fiber masses of the cellulose based fibers are not included in the skin side layer and are included in the clothing side layer. In a case in which the nonwoven fabric of the present disclosure has a three-layer structure of a skin side layer, a middle layer and a clothing side layer, preferably, the fiber masses of the cellulose based fibers are not included in the skin side layer and are included in the middle layer and/or the clothing side layer.

This configuration is preferable from the view point of the difficulty of the fiber masses to drop out of the nonwoven fabric. Further, since it is difficult for the liquid which is absorbed and retained by the fiber masses of the cellulose based fibers to come in contact with the skin of the wearer, it is difficult to make the wearer sense the wet state, and to give the wearer uncomfortable feeling. Still further, since the skin side layer of the nonwoven fabric of the present disclosure does not include the cellulose based fibers, the deterioration of the texture, the deterioration of the softness, etc., which may be caused by the cellulose based fibers, for example, cotton, can be prevented, whereby the nonwoven fabric of the present disclosure can have excellent texture and softness.

In the first embodiment and the second embodiment, the nonwoven fabric 13 is a flat nonwoven fabric in which both of the first surface 15 the second surface 17 are flat, however, the nonwoven fabric of the present disclosure may be a shaped nonwoven fabric which has a shaped structure.

As an embodiment in which the nonwoven fabric of the present disclosure is a shaped nonwoven fabric which has a shaped structure, the one in which the nonwoven fabric includes a plurality of protruded portions which protrude from the first surface to the second surface (protruding in the second surface), and a plurality of dented portions which are dented from the second surface to the first surface (being dented in the first surface), and each of the plurality of protruded portions and each of the plurality of dented portions are overlapped with each other in the thickness direction of the nonwoven fabric, may be mentioned. Accordingly, in a case in which the absorbent body is disposed on the second surface side (in a case in which the second surface of the shaped nonwoven fabric is joined to the liquid impermeable sheet), the dented portions can form the above described separated regions between the absorbent body.

FIGS. 5 to 9 are views for explaining the absorbent article 101 which includes the shaped nonwoven fabric 113 and the shaped nonwoven fabric 113 as the liquid permeable sheet 103, according to another embodiment (the third embodiment) of the present disclosure.

Figure 5:
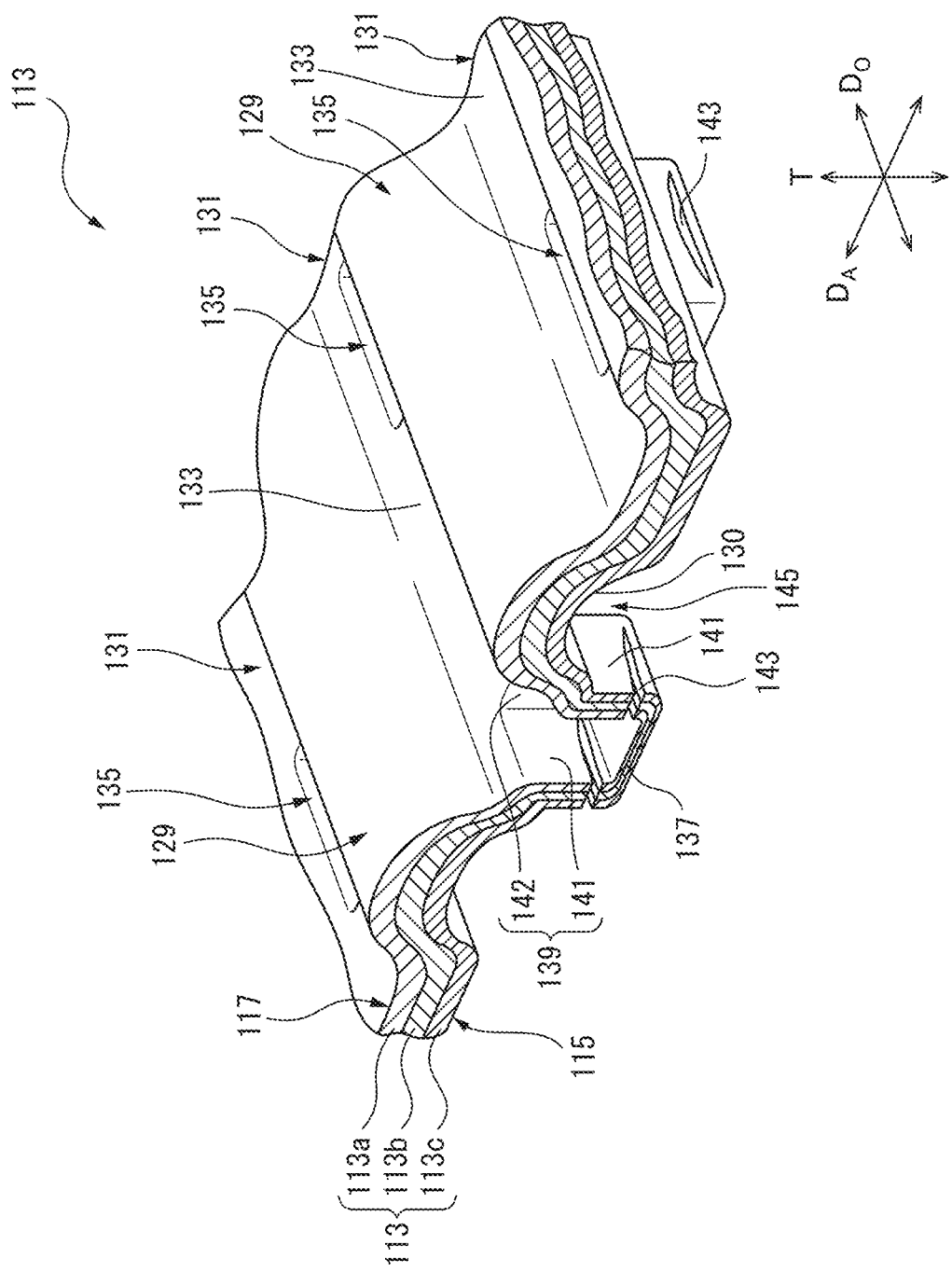
FIG. 5 is a perspective view of a shaped nonwoven fabric 113 according to a third embodiment.
Figure 6:
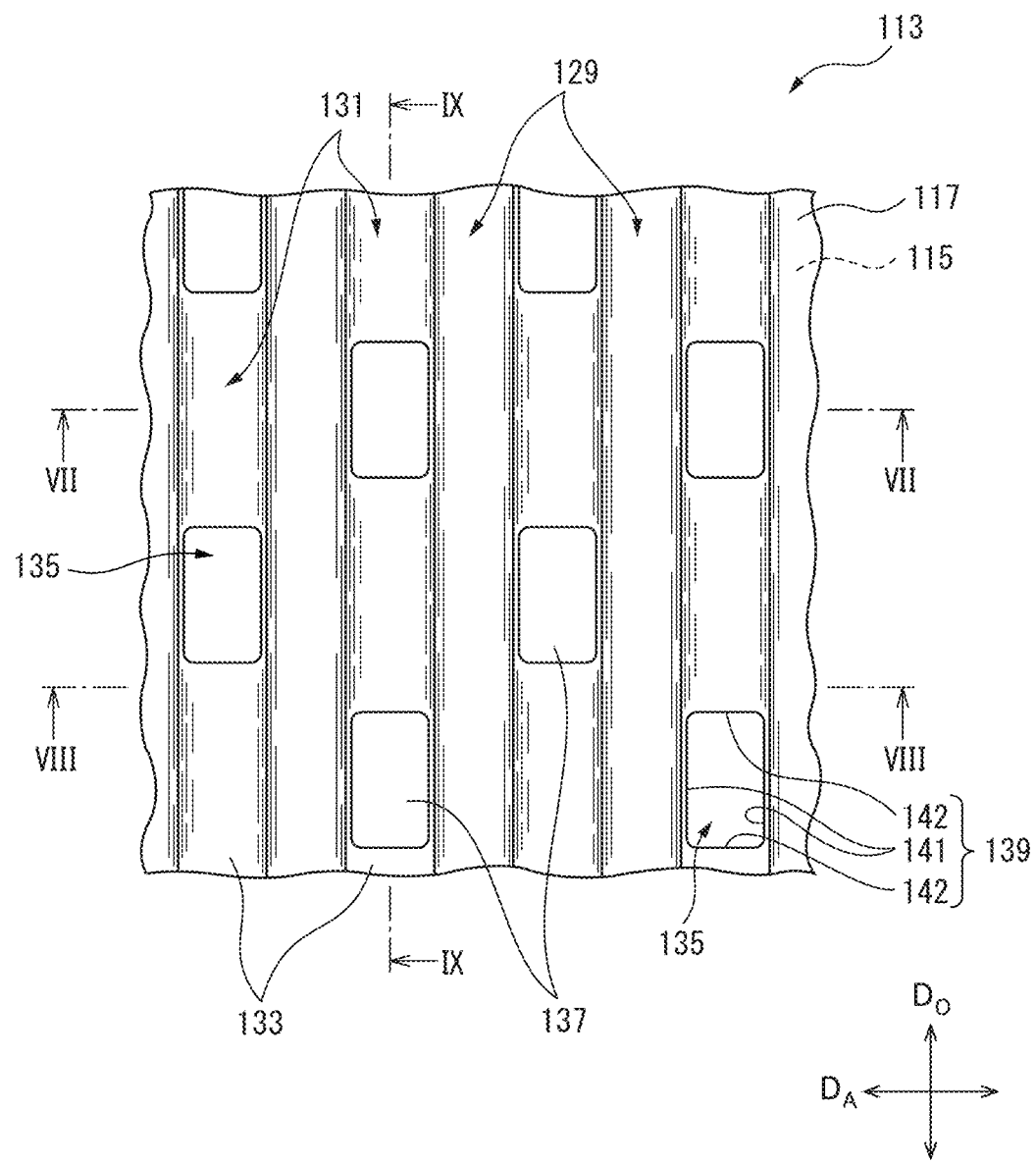
FIG. 6 is a plan view of the shaped nonwoven fabric 113.
Figure 7:
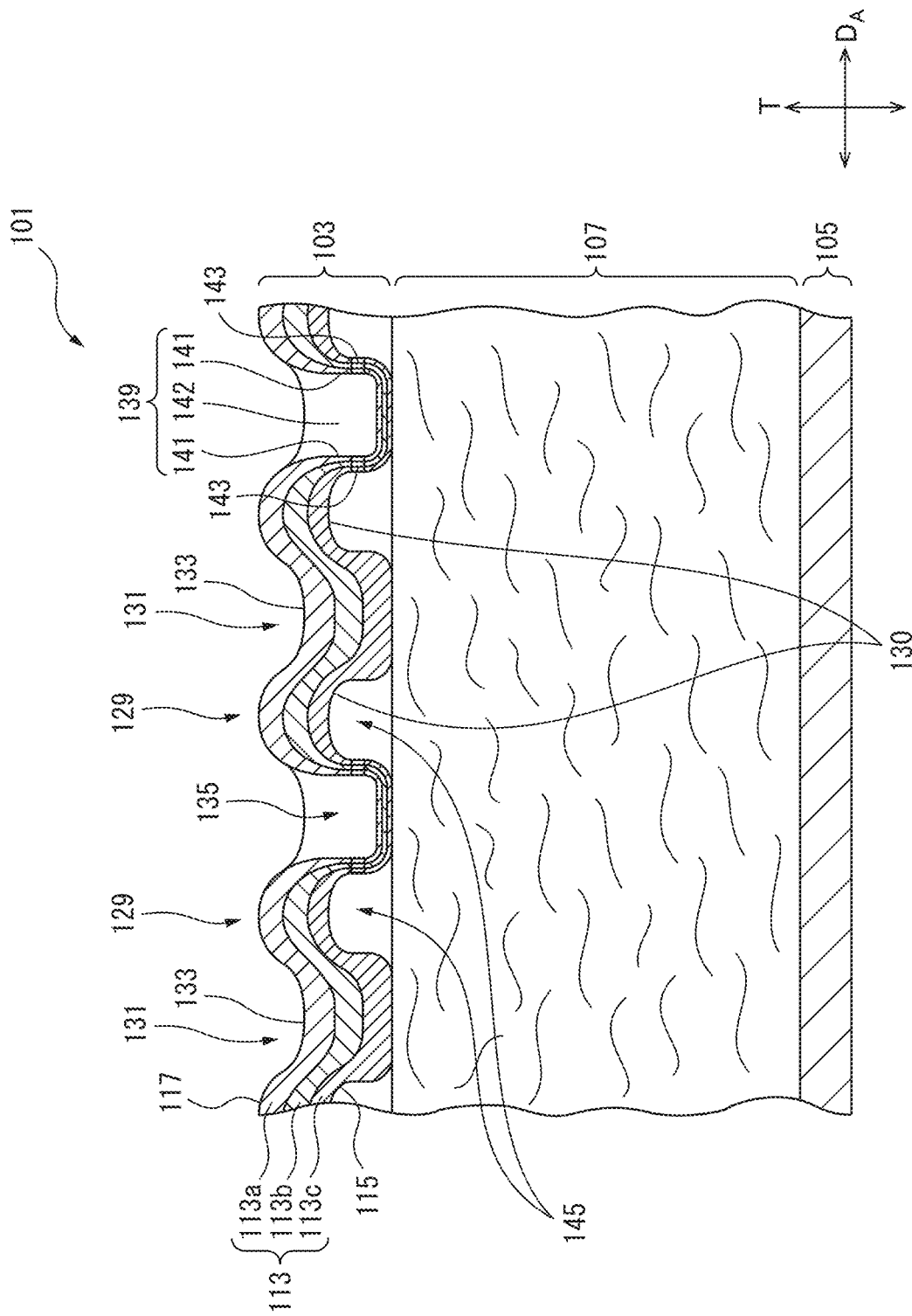
FIG. 7 is a sectional view along VII-VII cross section of FIG. 6.
Figure 8:
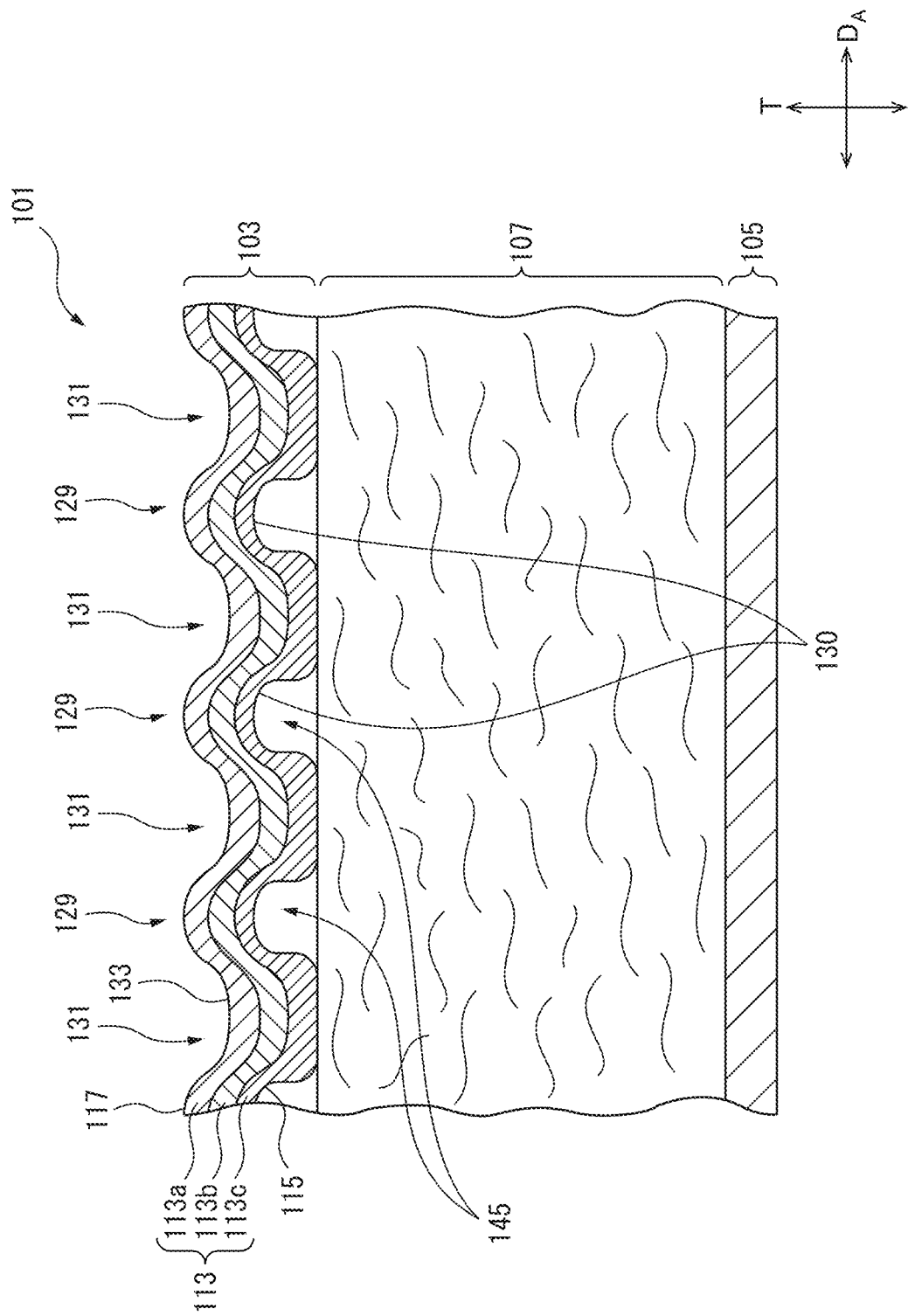
FIG. 8 is a sectional view along VIII-VIII cross section of FIG. 6.
Figure 9:
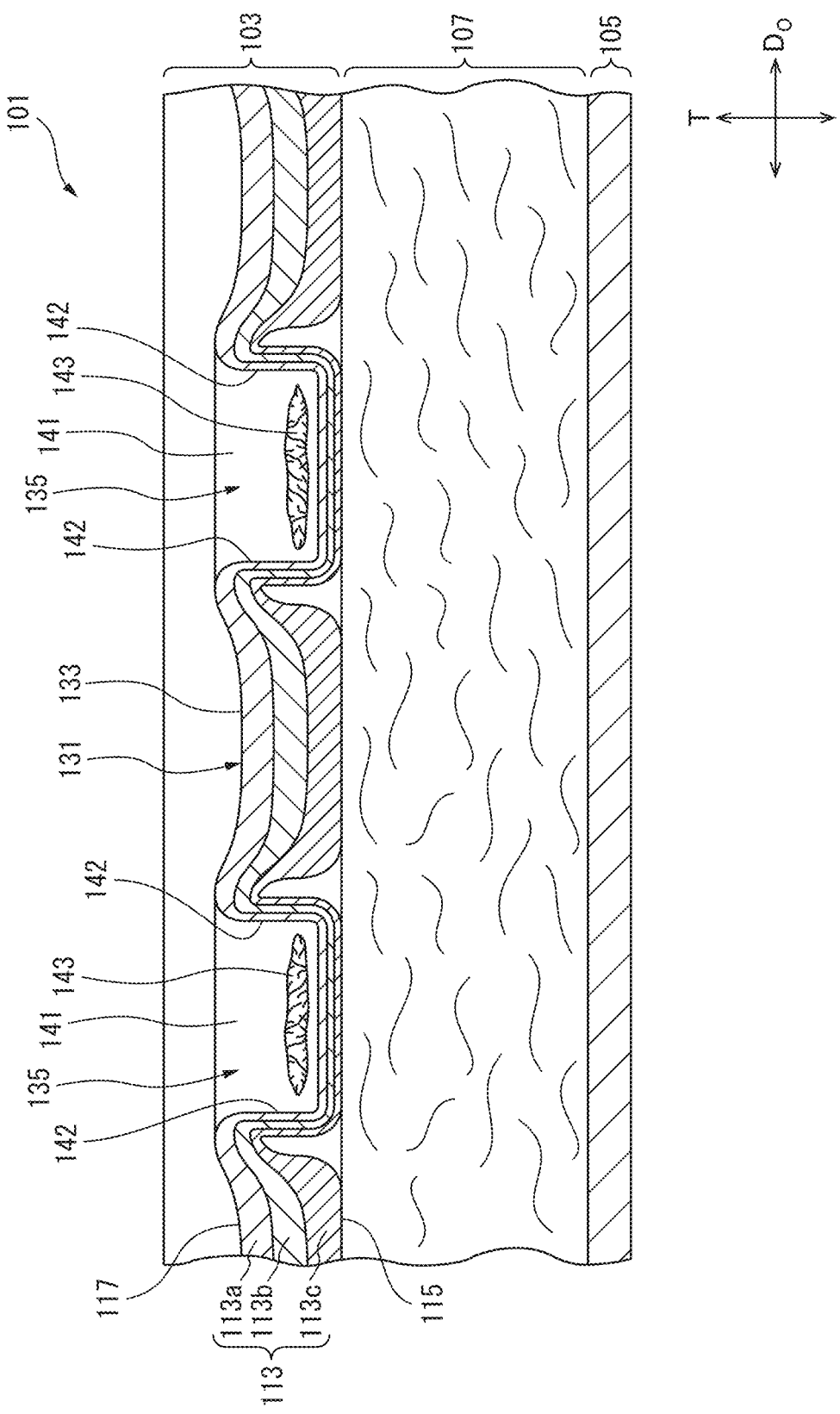
FIG. 9 is a sectional view along IX-IX cross section of FIG. 6.

To be more specific, FIG. 5 is a perspective view of the shaped nonwoven fabric 113 according to the third embodiment. FIG. 6 is a plan view of the shaped nonwoven fabric 113. FIG. 7 is a sectional view along VII-VII cross section of FIG. 6. FIG. 8 is a sectional view along VIII-VIII cross section of FIG. 6. FIG. 9 is a sectional view along IX-IX cross section of FIG. 6. Incidentally, FIGS. 5 and 6 show the shaped nonwoven fabric 113, and FIGS. 7 to 9 show the absorbent article 101.

The shaped nonwoven fabric 113 has a three-layer structure of the skin side layer 113a, the clothing side layer 113c, and the middle layer 113b which is present between the skin side layer 113a and the clothing side layer 113c. The skin side layer 113a is formed by thermoplastic resin fibers, and each of the middle layer 113b and the clothing side layer 113c is formed by thermoplastic resin fibers and cellulose based fibers at least a portion of which configuring the plurality of fiber masses.

The shaped nonwoven fabric 113 (the liquid permeable sheet 103) includes the first surface 115 which configures the surface on the absorbent body 107 side and the second surface 117 which configures the skin contact surface.

In the shaped nonwoven fabric 113, each of the plurality of protruded portions forms, in the second surface 117, the ridge portion 129 which protrudes in the direction from the first surface 115 to the second surface 117 and extends in the one direction $D_O$. Further, the shaped nonwoven fabric 113 includes, in the first surface 115, the plurality of dented portions 130 which are dented in the direction from the second surface 117 to the first surface 115, along the ridge portions 129. Incidentally, each of the plurality of ridge portions 129 and each of the plurality of dented portions 130 are overlapped with each other in the thickness direction T of the shaped nonwoven fabric 113.

The shaped nonwoven fabric 113 includes, between the two ridge portions 129 which are adjacent to each other in the other direction $D_A$ orthogonal to the one direction $D_O$, the plurality of groove portions 131 each of which including the groove bottom portion 133. Each of the plurality of groove portions 131 includes, in the groove bottom portion 133, the plurality of recessed portions 135 which are disposed intermittently in the one direction $D_O$ and are recessed in the direction from the second surface to the first surface, each of which including the bottom portion 137.

Each of the plurality of recessed portions 135 is configured by the bottom portion 137 and the circumferential wall portion 139 which connects the groove bottom portion 133 the bottom portion 137. The circumferential wall portion 139 is partitioned into the pair of first circumferential wall portions 141 which are disposed along the one direction $D_O$, and the pair of second circumferential wall portions 142 which are disposed along the other direction $D_A$.

Each of the pair of first circumferential wall portions 141 which are disposed along the one direction $D_O$ includes the hole portion 143 which penetrates from the first surface 115 to the second surface 117.

In each of the plurality of recessed portions 135, the bottom portion 137 has the highest fiber density among the shaped nonwoven fabric 113. Accordingly, the moisture (gas) and liquid which are released from the absorbent body is caught by the bottom portion 137 at which the fiber density is high, whereby it is difficult for the moisture (gas) and liquid which are released from the absorbent body to be transmitted to the wearer's side from the absorbent body 107 beyond the bottom portion 137 of the liquid permeable sheet 103 (the shaped nonwoven fabric 113).

The liquid permeable sheet 103 (the shaped nonwoven fabric 113) includes the separated regions 145 between the absorbent body 107. To be more specific, the liquid permeable sheet 103 (the shaped nonwoven fabric 113) includes the separated regions 145 between the dented portions 130 and the absorbent body 107. Accordingly, when the liquid which is absorbed and retained by the absorbent body 107 is released from the absorbent body 107 to the wearer's side as moisture by evaporation, etc., since the cellulose based fibers (which are not shown) included in the middle layer 113b and the clothing side layer 113c of the liquid permeable sheet 103 (the shaped nonwoven fabric 113) absorb and retain the moisture, and further, the moisture state is kept within the separated regions 145 (that is, the separated regions 145 are in a high humidity state), a state like a gas-liquid equilibrium is to be established between the moisture (gas phase) within the separated regions 145 and the liquid (liquid phase) absorbed and retained by the absorbent body 107, whereby the moisture is suppressed from being released any further from the absorbent body 107. Accordingly, it is difficult for the wearer to sense steaming feeling.

In the liquid permeable sheet 103 (the shaped nonwoven fabric 113), the dented portions 130 are not joined to the absorbent body 107, and portions on the first surface 115 side of the groove portions 131 are joined to the absorbent body 107 by an adhesive agent (which is not shown). Further, in the shaped nonwoven fabric 113, portions on the first surface 115 side of the groove bottom portions 133 of the groove portions 131 are joined to the absorbent body 107 by an adhesive agent (which is not shown).

The liquid permeable sheet 103 (the shaped nonwoven fabric 113) has a curved shape of being protruded toward the second surface 117 side at the ridge portions 129, and a curved shape of being protruded toward the first surface 115 side at the groove portions 131. That is, the shaped nonwoven fabric has a cross section of a substantially wavy shape in which ridge portions and groove portions are alternately repeated in the other direction $D_A$.

In the embodiment in which the nonwoven fabric of the present disclosure is a shaped nonwoven fabric, the shaped structure may be present not only in the overlapped region of being overlapping with the absorbent body in the thickness direction of the absorbent article, but also in the non-overlapped region of not being overlapping with the absorbent body in the thickness direction of the absorbent article. Accordingly, the moisture which is released from the edges of the absorbent body can be sealed in the separated regions.

The pitch of the ridge portions 129 in the other direction $D_A$ is preferably 0.25 to 5.0 mm, more preferably 0.5 to 3.0 mm, and even more preferably 0.75 to 2.0 mm. When the above described pitch is less than 0.25 mm, there may be cases in which the shaped structure of the shaped nonwoven fabric is too fine that the contact area between the shaped nonwoven fabric and the skin of the wearer cannot be reduced so much, and the texture of the shaped nonwoven fabric may be lowered. When the above described pitch is more than 5.0 mm, there may be cases in which it is difficult to obtain the soft texture which takes advantage of the shaped structure.

The height from the groove bottom portions 133 of the groove portions 131 to the top portions of the ridge portions 129 (the height of the nonwoven fabric in the thickness direction T) is preferably 0.25 to 5.0 mm, more preferably 0.5 to 3.0 mm, and even more preferably 0.75 to 2.0 mm. When the above described height is less than 0.25 mm, there may be cases in which the protrusions of the ridge portions are small, and it is difficult to obtain the soft texture which takes advantage of the shaped structure. When the above described height is more than 5.0 mm, there may be cases in which the protrusions of the ridge portions are large, and it is difficult to obtain the soft texture.

The depth of the recessed portions 135, in other words, the distance from the groove bottom portions 133 of the groove portions 131 to the bottom portions 137 of the recessed portions 135 is preferably 0.05 to 2.0 mm, more preferably 0.075 to 1.5 mm, and even more preferably 0.1 to 1.0 mm. When the above described distance is less than 0.05 mm, there is a tendency that it is difficult to secure the rigidity of the bottom portions 137, whereby the strength of the nonwoven fabric in the thickness direction may be insufficient. On the other hand, when the above described distance is more than 2.0 mm, there is a tendency that the strength of the shaped nonwoven fabric in the thickness direction may be insufficient.

Since the shaped nonwoven fabric 113 according to the third embodiment has a certain shaped structure, that is, a structure which includes the plurality of ridge portions 129, the plurality of groove portions 131 having the groove bottom portions 133, and the plurality of recessed portions 135 which are intermittently disposed between the groove bottom portions 133, the force in the thickness direction T of the shaped nonwoven fabric 113 applied from the second surface 117 side of the shaped nonwoven fabric 113 can be buffered, and in a case in which the force in the thickness direction T is applied so that the shaped structure is temporarily crushed, it is easy to restore the shaped structure when the force is removed.

Further, since the shaped nonwoven fabric 113 according to the third embodiment has the certain shaped structure, and can buffer the force in the thickness direction T of the shaped nonwoven fabric 113 applied from the second surface 117 side of the shaped nonwoven fabric 113, even when the shaped nonwoven fabric 113 includes cellulose based fibers, for example, cotton, sufficient softness can be secured.

The shaped nonwoven fabric according to the third embodiment may be manufactured according to the methods described in Japanese Patent Publication Nos. 5829326, 5829327, and 5829349.

In the nonwoven fabric of the present disclosure, the thermoplastic resin fibers are not particularly limited as long as the thermoplastic resin fibers are made of thermoplastic resins, and as the thermoplastic resins, for example, olefinic resins such as polyethylene (PE), polypropylene (PP), ethylene-vinyl acetate copolymer (EVA); polyester resins such as polyethylene terephthalate (PET), polylactic acid (PLA); polyamide resins such as 6-nylon; and arbitrary combinations thereof may be mentioned. The above described thermoplastic resin fibers may be hydrophilic or hydrophobic, and may be hydrophilized by a hydrophilizing agent.

The fineness of the above described thermoplastic resin fibers is not particularly limited, however, from the viewpoint of the strength, the softness, the texture, and the liquid permeability of the nonwoven fabric, the fineness is within the range generally of 1.1 to 8.8 dtex, and within the range preferably of 1.5 to 4.6 dtex.

The average fiber length of the above described thermoplastic resin fibers is not particularly limited, however, from the viewpoint of the strength, the softness, and the liquid permeability of the nonwoven fabric, the average fiber length is within the range normally of 20 to 100 mm, and within the range preferably of 35 to 65 mm.

Further, in a case in which the nonwoven fabric of the present disclosure has a multiple-layer structure, the fiber diameter of the thermoplastic resin fibers included in the layer including the cellulose based fibers is preferably smaller than the fiber diameter of the thermoplastic resin fibers included in the layer not including the cellulose based fibers. It is easier for the thermoplastic resin fibers included in the layer including the cellulose based fibers having a small fiber diameter to be entangled with the cellulose based fibers of the layer including the cellulose based fibers and with the thermoplastic resin fibers of the layer not including the cellulose based fibers, and it is difficult for the interlayer peeling and delamination, etc., accompanied with the dissociation between the thermoplastic resin fibers and the cellulose based fibers to be caused, whereby the nonwoven fabric can retain excellent strength.

In the nonwoven fabric of the present disclosure, the cellulose based fibers are not particularly limited as long as the cellulose based fibers are fibers including cellulose, and for example, natural cellulose fibers, regenerated cellulose fibers, purified cellulose fibers, and semi-synthetic cellulose fibers may be mentioned.

As the above described natural cellulose fibers, vegetable fibers, for example, seed hair fibers (such as cotton), bark fibers (such as hemp), leaf vein fibers (such as Manila hemp), fruit fibers (such as palm) may be mentioned.

As the above described cotton, *Gossypium hirsutum* cotton (for example, Upland cotton), *Gossypium barbadense* cotton, *Gossypium arboreum* cotton, and *Gossypium herbaceum* cotton may be mentioned.

Further, the above described cotton may be organic cotton, or Pre Organic Cotton (trademark).

The organic cotton means cotton which is certified by GOTS (Global Organic Textile Standard).

As the above described regenerated cellulose fibers, fibers of rayon, for example, viscose rayon obtained from viscose, polynosic and modal, copper ammonium rayon obtained from copper ammonium salt solution of cellulose (which is also referred to as "cupra"), etc., may be mentioned.

As the above described purified cellulose fibers, lyocell, and to be more specific, fibers made of pulp being dissolved in an aqueous solution of N-methylmorpholine N-oxide to prepare a spinning solution (dope), and being extruded into a dilute solution of N-methylmorpholine N-oxide. The above described purified cellulose fibers are commercially available for example as Tencel (trademark).

As the above described semi-synthetic fibers, fibers of semi-synthetic cellulose, for example, acetate fibers such as triacetate and diacetate, etc., may be mentioned.

In the nonwoven fabric of the present disclosure, the cellulose based fibers preferably have a shorter average fiber length than the thermoplastic resin fibers. This is because, at the time when the nonwoven fabric is manufactured, it is easier to suppress the opening of cellulose based fibers and to form the fiber masses of the cellulose based fibers, and as a result, it is easier for the fiber masses of the cellulose based fibers to be present in a state of being distributed in the matrix of the thermoplastic resin fibers within the nonwoven fabric.

The above described cellulose based fibers preferably have a shorter average fiber length than the thermoplastic resin fibers, and the average fiber length of the cellulose based fibers is more preferably 10 to 50 mm, and is even more preferably 20 to 28 mm Incidentally, in a case in which the cellulose based fibers are cotton, cotton with an average fiber length of 20.6 to 25.4 mm is referred to as medium fiber cotton, and cotton with an average fiber length of 26.2 to 27.8 mm is referred to as medium long fiber cotton.

The above described cellulose based fibers are preferably natural cellulose fibers, more preferably cotton, and are even more preferably *Gossypium hirsutum* cotton. This is from the viewpoint of obtaining feeling of security by natural materials, and obtaining absorbent property and retaining property of liquid.

In the present disclosure, an average fiber length of fibers is measured in accordance with "A7.1.1 Method A (Standard method) A method of measuring a length of individual fibers on a scaled glass plate" of "A7.1 Measurement of a fiber length" of JIS L 1015:2010 Annex A.

Incidentally, the above described method is a test method which corresponds to ISO 6989 issued in 1981.

The nonwoven fabric of the present disclosure includes the cellulose based fibers with a proportion of preferably 3 to 35% by mass, more preferably 3 to 20% by mass, and even more preferably 3 to 10% by mass. This is from the viewpoint of making it easier for the fiber masses of the cellulose based fibers to absorb and retain intensively (spotwise) the moisture which has permeated the nonwoven fabric and is about to be discharged from the absorbent body to the space between the absorbent article and the wearer, through the gap portions, whereby in the plane direction of the nonwoven fabric, making the area of the portions which retain the moisture smaller (spotwise), and reducing the amount of moisture which permeates the nonwoven fabric and is discharged from the absorbent body to the space between the absorbent article and the wearer. Accordingly, the nonwoven fabric of the present disclosure makes it difficult for moisture from the absorbent body to permeate the space between the absorbent article and the wearer, and makes it difficult for steaming feeling to be sensed.

In a case in which the nonwoven fabric of the present disclosure is configured by thermoplastic resin fibers and cellulose based fibers, the nonwoven fabric includes the thermoplastic resin fibers and the cellulose based fibers with a proportion of preferably 65 to 97% by mass and 3 to 35% by mass, more preferably 80 to 97% by mass and 3 to 20% by mass, and even more preferably 90 to 97% by mass and 3 to 10% by mass.

Incidentally, the nonwoven fabric of the present disclosure may include a third fiber other than the thermoplastic resin fibers and the cellulose based fibers.

The nonwoven fabric of the present disclosure preferably has a joining point at which the thermoplastic resin fibers are joined to each other, at portions other than the fiber masses of the cellulose based fibers. As the above described joining point, a joining point by an adhesive agent, and a fusion point of the thermoplastic resin fibers, etc., may be mentioned.

Further, in the nonwoven fabric of the present disclosure, the cellulose based fibers may be included in portions other than the fiber masses of the cellulose based fibers, for example, in the matrix of the thermoplastic resin fibers.

In the absorbent article of the present disclosure, the liquid impermeable sheet preferably has a moisture permeability, and the liquid impermeable sheet has a moisture permeability more preferably of 1,500 to 4,500 $g/m^2/24$ h, even more preferably of 2,000 to 4,000 $g/m^2/24$ h, and still even more preferably of 2,500 to 3,800 $g/m^2/24$ h. This is from the viewpoint of discharging the moisture inside the absorbent article through the liquid impermeable sheet, whereby reducing the moisture inside the absorbent article and the moisture which is kept between the absorbent article and the wearer.

As the above described moisture permeability, the value which is measured in accordance with "The moisture permeability testing method of a moisture-proof packaging material (the cup method)" of JIS Z 0208: 1976 is adopted, however, the above described moisture permeability is different from JIS Z 0208: 1976 in the following points.

(i) in the moisture permeable cup, 20 g of water is filled instead of calcium chloride (ii) the moisture permeability is measured in a constant temperature and humidity chamber which has a temperature of 40° C. and a relative humidity of 60%

(iii) after leaving still the cup for 24 hours, not the mass increase of the cup but the mass decrease of 20 g of water (the discharged amount) is measured As the above described liquid impermeable sheet, a film such as a polyolefin based film, and a nonwoven fabric such as a nonwoven fabric made of spunbond or spun lace, etc., may be mentioned. In a case in which the liquid impermeable sheet is a film, the film preferably has a moisture permeability, and for example, the film is preferably a moisture permeable film. Further, the above described liquid impermeable sheet preferably does not have a liquid permeability.

The nonwoven fabric of the present disclosure has a basis weight in a range generally of 10 to 100 $g/m^2$, preferably of 15 to 75 $g/m^2$, and more preferably of 20 to 50 $g/m^2$. This is from the viewpoint of the effect of the present disclosure.

Further, the nonwoven fabric of the present disclosure, although not particularly limited, has a thickness generally of 0.1 to 5.0 mm, preferably of 0.5 to 3.0 mm, and more preferably of 0.8 to 2.0 mm. This is from the viewpoint of the effect of the present disclosure. Incidentally, in a case in which the nonwoven fabric of the present disclosure is a shaped nonwoven fabric, the above described thickness means the thickness of the nonwoven fabric before being shaped.

In the present description, the thickness of the nonwoven fabric (mm) is measured in the following manner.

FS-60DS [the measurement surface of 44 mm (in diameter), the measurement pressure of 3 $g/cm^2$] manufactured by Daiei Kagaku Seiki MFG Co., Ltd. is prepared, five different portions of the nonwoven fabric are applied with pressure under the standard condition (the temperature of 23±2° C., the relative humidity of 50±5%), the thickness of each of the portions ten seconds after the pressure is applied is measured, and the average value of the five measurement values is to be the thickness of the nonwoven fabric.

In the nonwoven fabric of the present disclosure, the fiber masses of the cellulose based fibers are preferably distributed within the nonwoven fabric, and the nonwoven fabric of the present disclosure more preferably includes the matrix which configures the nonwoven fabric and the fiber masses of the cellulose based fibers which are distributed in the matrix. This is because when liquid such as excretory fluid, etc., which is absorbed and retained by the absorbent body is discharged from the absorbent body as moisture, the moisture can be absorbed and retained intensively (spotwise) at the fiber masses of the cellulose based fibers, and in the plane direction of the nonwoven fabric, the area of the portions which absorb and retain the moisture can be made smaller (spotwise), whereby the amount of moisture to be discharged to the wearer's side can be suppressed to the minimum. As a result, the moisture which is discharged from the absorbent body can be effectively sealed by the gap portions which are adjacent to the fiber masses and by the separated regions.

Incidentally, the above described matrix can be configured by the fibers included in the nonwoven fabric of the present disclosure, and for example, can be configured by thermoplastic resin fibers and cellulose based fibers, and preferably is configured by thermoplastic resin fibers. This is from the viewpoint of the effect of the present disclosure.

The nonwoven fabric of the present disclosure, for example, a nonwoven fabric which has a two-layer structure of a skin side layer which has a skin contact surface and a clothing side layer which is disposed on the further clothing side than the skin side layer, may be manufactured in accordance with the following manufacturing method. Incidentally, the following manufacturing method is one example of the manufacturing method of the nonwoven fabric of the present disclosure, and the nonwoven fabric of the present disclosure may be manufactured by an arbitrary method.

(1) A nonwoven fabric manufacturing apparatus is prepared which includes a conveying belt that is capable of conveying a sheet-like member while adjusting the tension thereof, and further includes, along the conveying belt, a first stage carding machine, a second stage carding machine, a heating machine of an air-through method, a compressing machine including a pair of anvil rolls, and a bulk recovering machine (a thickness recovering machine) including a heating means, in this order.

(2) Core sheath-type thermoplastic resin fibers and cellulose based fibers are supplied to the first stage carding machine so as to open the thermoplastic resin fibers and the cellulose based fibers, and a first web which may form the clothing side layer is formed on the conveying belt. Incidentally, by setting the average fiber length of the cellulose based fibers shorter than the average fiber length of the thermoplastic resin fibers, the opening of the cellulose based fibers can be suppressed and it is easier for the fiber masses of the cellulose based fibers to remain in the first web.

(3) The core sheath-type thermoplastic resin fibers and cellulose based fibers are supplied to the second stage carding machine so as to open the thermoplastic resin fibers and the cellulose based fibers, and a second web which may form the skin side layer is stacked on the first web on the conveying belt, whereby the stacked web is formed.

(4) The stacked web is conveyed to the heating machine of an air-through method, and the stacked web is heated by a temperature which is higher than the melting point of the sheath portion of the core sheath-type thermoplastic resin fibers, so as to heat fuse the thermoplastic resin fibers with each other within the first web and the second web, whereby the nonwoven fabric to be processed is formed.

(5) The nonwoven fabric to be processed is compressed in the thickness direction thereof by using the pair of anvil rolls of the compressing machine, so that the thickness of the nonwoven fabric to be processed is compressed to, for example, approximately 10 to 40% (=100×the thickness of the compressed nonwoven fabric/the thickness of the nonwoven fabric to be processed), and the matrix which is mainly configured by the thermoplastic resin fibers, and the fiber masses of the cellulose based fibers are compressed, whereby the compressed nonwoven fabric is formed.

Incidentally, by winding the compressed nonwoven fabric on a roll, the compressed nonwoven fabric may be further compressed. In a case of winding the compressed nonwoven fabric on a roll, the compressed nonwoven fabric is preferably further compressed so that the thickness of the compressed nonwoven fabric is 30 to 50%.

(6) By adding tension in the conveying direction to the compressed nonwoven fabric rather strongly, the fusion portions which have been formed between the thermoplastic resin fibers and the fiber masses of the cellulose based fibers are cut, and the nonwoven fabric in which the fusion portions between the cellulose based fibers and the fiber masses of the are cut is formed.

(7) The nonwoven fabric in which the fusion portions between the cellulose based fibers and the fiber masses of the are cut is conveyed to the bulk recovering machine, and the above described nonwoven fabric is heated, so that the thickness of the above described nonwoven fabric is recovered to, for example, approximately 130 to 200% (=100×the thickness of the nonwoven fabric of the present disclosure/the nonwoven fabric in which the fusion portions between the cellulose based fibers and the fiber masses of the are cut), whereby gaps are formed between the thermoplastic resin fibers the thickness of which is easily recovered and the fiber masses the thickness of which is difficult to be recovered, and the nonwoven fabric of the present disclosure is formed.

Incidentally, in a case in which the nonwoven fabric of the present disclosure has a three-layer structure of a skin side layer which has a skin contact surface, a clothing side layer which is disposed on the clothing side and a middle layer which is present between the skin side layer and the clothing side layer, a third stage carding machine can be disposed between the second stage carding machine and the heating machine of an air-through method.

Incidentally, the forming method of the web of each layer is not limited to the above described method, and for example, a wet method can also be adopted. Further, the forming method of the nonwoven fabric is not limited to the above described method, and for example, a water flow entanglement method or a needle punching method, etc., may be adopted.

Further, after step (7), the shaping step of the nonwoven fabric may be provided in accordance with the methods described in Japanese Patent Publication Nos. 5829326, 5829327, and 5829349.

The nonwoven fabric of the present disclosure may be preferably used for a liquid permeable sheet of an absorbent article, and the above described absorbent article is not particularly limited, and for example, a disposable diaper, a urine removal pad, a sanitary napkin, a panty liner, etc., may be mentioned.

EXAMPLES

Hereinbelow, the present disclosure is explained by mentioning examples, however the present disclosure is not limited to these examples.

[Evaluation of Transpiration]

Manufacturing Example 1

<Manufacturing of the Nonwoven Fabric>

Two types of PET/PE core sheath-type composite fibers with different fineness (composite fibers A: fineness of 2.2 dtex, average fiber length of 45 mm, composite fibers B: fineness of 1.7 dtex, average fiber length of 45 mm), and *Gossypium hirsutum* cotton (average fiber length of 27 mm) were supplied to the first stage carding machine, and these fibers were opened, whereby the first web (the clothing side layer, basis weight: 13 g/m$^2$, basis weight of the composite fibers A and the composite fibers B: 10 g/m$^2$, basis weight of *Gossypium hirsutum* cotton: 3 g/m$^2$) was formed.

PET/PE core sheath-type composite fibers (fineness of 2.8 dtex, average fiber length of 45 mm) as the thermoplastic resin fibers were supplied to the second stage carding machine, the PET/PE core sheath-type composite fibers were opened, and the second web (the skin side layer, basis weight: 20 g/m$^2$) were formed on the first web so as to form the stacked web.

The stacked web was conveyed to the heating machine of an air-through method, and the PET/PE core sheath-type composite fibers within each web and between the web were heat fused inside the heating machine, whereby the nonwoven fabric to be processed No. 1 was obtained.

The nonwoven fabric to be processed No. 1 was compressed in the thickness direction thereof by the pair of anvil rolls, so that the thickness is compressed to approximately 20%. Subsequently, tension in the plane direction was applied to the nonwoven fabric to be processed No. 1, and the thickness thereof was recovered by applying heat, whereby the nonwoven fabric No. 1 was formed.

Figure 10:
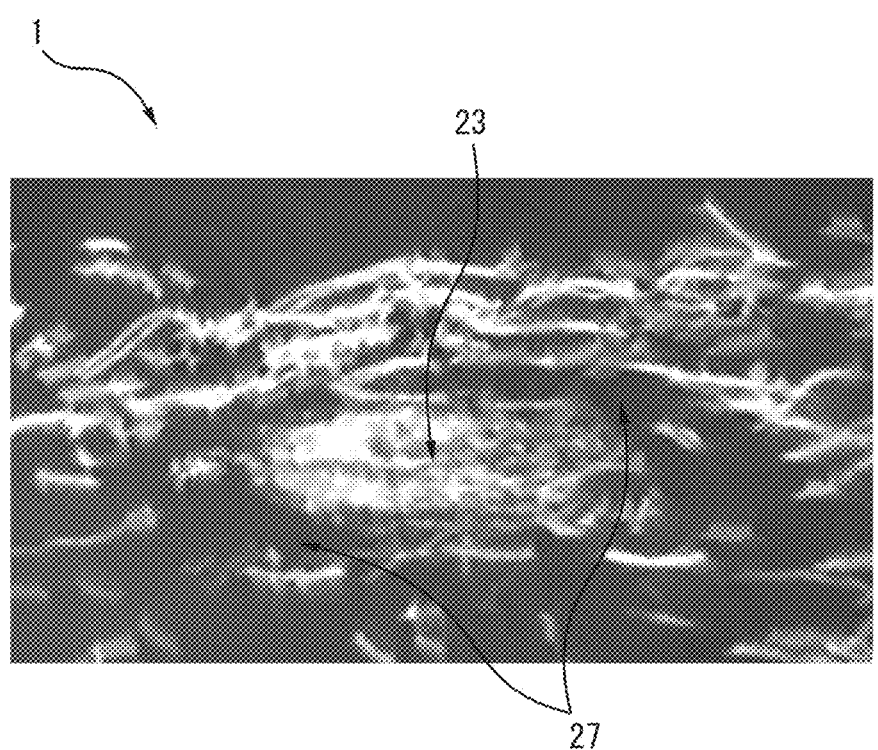
FIG. 10 is an image of a nonwoven fabric No 1 manufactured in the manufacturing example 1 photographed by a three-dimensional measurement X-ray CT apparatus.

The nonwoven fabric No. 1 was scanned by a three-dimensional measurement X-ray CT apparatus (TDM-1000-IS/SP manufactured by Yamato Scientific co., ltd.), and a three-dimensional image in the vicinity of the fiber masses was obtained. Such an image is shown in FIG. 10. As shown in FIG. 10, it can be understood that the gap portions 27 are present adjacently to the fiber masses 23.

<Manufacturing of the Disposable Diaper>

Absorbent materials in which pulp with a basis weight of 220 g/m$^2$ and super absorbent polymers (SAP) with a basis weight of 156 g/m$^2$ were mixed were wrapped by a tissue with a basis weight of 10 g/m$^2$, whereby the absorbent body was obtained. The nonwoven fabric No. 1 was joined to one surface of the obtained absorbent body as the liquid permeable sheet so that the first surface (which is the clothing side layer formed by the first web) came in contact with the absorbent body, and a moisture permeable film with basis weight of 15 g/m$^2$ was joined to the other surface of the absorbent body as the liquid impermeable sheet, whereby a stacked body was obtained. Incidentally, an adhesive agent of a hot melt type (the application amount: 3 g/m$^2$) was used for the joining.

Further, the obtained stacked body was cut into a predetermined shape of a disposable diaper, whereby the disposable diaper No. 1 was made.

Manufacturing Example 2

The nonwoven fabric No. 1 which was manufactured in the Manufacturing example 1 was subjected to shaping processing in accordance with the method described in Japanese Patent Publication No. 5829326, whereby the nonwoven fabric No. 2 was manufactured.

Subsequently, the disposable diaper No. 2 was manufactured in the same manner as the Manufacturing example 1 except for using the nonwoven fabric No. 2 instead of the nonwoven fabric No. 1. Incidentally, the nonwoven fabric No. 2 was joined so that the first surface (which is the clothing side layer formed by the first web) came in contact with the absorbent body.

Comparative Manufacturing Example 1

The nonwoven fabric No. 3 and the disposable diaper No. 3 were made in the same manner as the Manufacturing example 1 except for forming the first web (basis weight: 10 g/m$^2$) by a mixture of two types of PET/PE core sheath-type composite fibers with different fineness (composite fibers A with fineness of 2.2 dtex and average fiber length of 45 mm, and composite fibers B with fineness of 1.7 dtex and average fiber length of 45 mm).

Examples 1, 2 and Comparative Example 1

In the disposable diapers Nos. 1 to 3, after artificial urine was absorbed, the transpiration rate for every predetermined amount of time (% by mass) was evaluated. The results are shown in Table 1.

[Measuring Method of the Transpiration Rate]

(1) In order to eliminate the influence from the surrounding environment, the sample is left still in a constant temperature and humidity tank with a temperature of 20° C. and a relative humidity of 60% RH for 5 days (120 hours).

(2) The sample is removed out from the constant temperature and humidity tank, and the initial mass of the sample: $A_0$ (g) is measured.

(3) The sample is expanded on a test bed with a horizontal surface so that the liquid permeable sheet is to be the upper surface, and a cylinder with an inner diameter of 60 mm is placed on the liquid permeable sheet.

(4) In the cylinder, 80 mL of artificial urine is dropped in 10 seconds.

Incidentally, the artificial urine is prepared by dissolving 200 g of urea, 80 g of sodium chloride, 8 g of magnesium sulfate, 3 g of calcium chloride, and approximately 1 g of a dye (blue No. 1) in 10 L of ion exchanged water.

(5) After confirming that all of the artificial urine inside the cylinder has been absorbed, the cylinder is removed from above the liquid permeable sheet, and the mass of the sample after absorbing the artificial urine: $A_1$ (g) is immediately measured.

(6) The sample after absorbing the artificial urine is left under a certain environment, and the masses of the sample: $W_1$, $W_3$, $W_5$, $W_8$ and $W_{21}$ (g), after 1 hour, 3 hours, 5 hours, 8 hours, and 21 hours, respectively from the point at which the cylinder was removed from above the top sheet in the above described (5) are measured.

(7) The transpiration rates of the sample: $E_1$, $E_3$, $E_5$, $E_8$ and $E_{21}$ (% by mass) for each elapsed time are calculated by the following formula (1).

$$E_N (\% \text{ by mass}) = 100 \times (A_1 - W_N)/(A_1 - A_0)$$

(in the formula, N stands for 1, 3, 5, 8 or 21)

TABLE 1

| | | Example No. | | |
|---|---|---|---|---|
| | | Example 1 | Example 2 | Comparative Example 1 |
| Disposable diaper No. | | No. 1 | No. 2 | No. 3 |
| Liquid permeable sheet | Nonwoven fabric No. | No. 1 | No. 2 | No. 3 |
| | Skin side layer (the second surface) | PET/PE composite fibers | PET/PE composite fibers | PET/PE composite fibers |
| | Basis weight (g/m$^2$) | 20 | 20 | 20 |
| | Clothing side layer (the first surface) | 2 types of PET/PE composite fibers + cotton | 2 types of PET/PE composite fibers + cotton | 2 types of PET/PE composite fibers |
| | Basis weight (g/m$^2$) | 10 + 3 | 10 + 3 | 10 |
| | Total basis weight (g/m$^2$) | 33 | 33 | 30 |
| | Shaping processing | Not performed | Performed | Not performed |
| Transpiration rate (%) | 1 hour later | 2.1 | 1.4 | 2.4 |
| | 3 hours later | 4.2 | 3.5 | 4.7 |
| | 5 hours later | 7.3 | 6.8 | 7.8 |
| | 8 hours later | 10.3 | 9.2 | 12.0 |
| | 21 hours later | 28.9 | 26.4 | 36.4 |

As shown in Table 1, in the disposable diapers Nos. 1 and 2, it could be understood that the transpiration rate after the artificial urine was absorbed was lower and it was difficult for the wet state, steaming, etc., to occur, compared to the disposable diaper No. 3. Especially, in the disposable diapers Nos. 1 and 2, it could be understood that the transpiration rates after 8 hours and after 21 hours from the absorption of the artificial urine were low, and it was difficult for the wet state and steaming to occur for a long period of time.

[Evaluation of Rewetting Property]

Manufacturing Example 3

<Manufacturing of the Nonwoven Fabric>

Two types of PET/PE core sheath-type composite fibers with different fineness (composite fibers A: fineness of 2.2 dtex, average fiber length of 45 mm, composite fibers B: fineness of 1.7 dtex, average fiber length of 45 mm) were supplied to the first stage carding machine, and the PET/PE core sheath-type composite fibers were opened, whereby the first web (the clothing side layer, basis weight: 10 g/m$^2$) was formed.

PET/PE core sheath-type composite fibers (fineness of 2.8 dtex, average fiber length of 45 mm) as the thermoplastic resin fibers, and *Gossypium hirsutum* cotton (average fiber length of 27 mm) were supplied to the second stage carding machine, these fibers were opened, and the second web (the middle layer, basis weight of the PET/PE core sheath-type composite fibers: 9 g/m$^2$, basis weight of *Gossypium hirsutum* cotton: 1 g/m$^2$) were formed on the first web so as to form the stacked web.

PET/PE core sheath-type composite fibers (fineness of 2.8 dtex, average fiber length of 45 mm) as the thermoplastic resin fibers were supplied to the third stage carding machine, the PET/PE core sheath-type composite fibers were opened, and the third web (basis weight of the PET/PE core sheath-type composite fibers: 10 g/m$^2$) were formed on the second web so as to form the stacked web.

The stacked web was conveyed to the heating machine of an air-through method, and the PET/PE core sheath-type composite fibers within each web and between the web were heat fused inside the heating machine, whereby the nonwoven fabric to be processed No. 4 was obtained.

The nonwoven fabric to be processed No. 4 was compressed in the thickness direction thereof by the pair of anvil rolls, so that the thickness is compressed to approximately 20%. Subsequently, tension in the plane direction was applied to the nonwoven fabric to be processed No. 4, and the thickness thereof was recovered by applying heat, whereby the nonwoven fabric No. 4 was formed.

<Manufacturing of the Disposable Diaper>

Absorbent materials in which pulp with a basis weight of 220 g/m$^2$ and super absorbent polymers (SAP) with a basis weight of 155 g/m$^2$ were mixed were wrapped by an SMMS nonwoven fabric with a basis weight of 10 g/m$^2$, whereby the absorbent body was obtained. The nonwoven fabric No. 4 was joined to one surface of the obtained absorbent body as the liquid permeable sheet so that the first surface (which is the clothing side layer formed by the first web) came in contact with the absorbent body, and a moisture permeable film with basis weight of 15 g/m$^2$ was joined to the other surface of the absorbent body as the liquid impermeable sheet, whereby the disposable diaper No. 4 was made.

Manufacturing Example 4

The nonwoven fabric No. 4 which was manufactured in the Manufacturing example 3 was subjected to shaping processing in accordance with the method described in Japanese Patent Publication No. 5829326, whereby the nonwoven fabric No. 5 was manufactured.

Subsequently, the disposable diaper No. 5 was manufactured in the same manner as the Manufacturing example 3 except for changing the liquid permeable sheet and the exterior film from the nonwoven fabric No. 4 to the nonwoven fabric No. 5. Incidentally, the nonwoven fabric No. 5 was joined so that the first surface (which is the clothing side layer formed by the first web) came in contact with the absorbent body.

Comparative Manufacturing Example 1

The nonwoven fabric No. 6 was formed in the same manner as the Manufacturing example 3 except for changing the second web from the second web (basis weight of the PET/PE core sheath-type composite fibers: 9 g/m$^2$, basis weight of *Gossypium hirsutum* cotton: 1 g/m$^2$) to the second web (basis weight of the PET/PE core sheath-type composite fibers: 10 g/m$^2$). Further, the disposable diaper No. 6 was manufactured in the same manner as the Manufacturing example 3 except for changing the liquid permeable sheet from the nonwoven fabric No. 4 to the nonwoven fabric No. 6.

Examples 3, 4 and Comparative Example 2

The rewetting properties of the disposable diapers Nos. 4 to 6 were evaluated based on the following measuring method of the rewetting amount. The results are shown in Table 2.

[Measuring Method of the Rewetting Amount]

(1) The disposable diapers Nos. 4 to 6 are set to a U-shaped instrument the side view of which is substantially U-shaped. Incidentally, the absorbent article is set so that the central position of the absorbent body in the longitudinal direction matches the central portion of the U-shaped instrument (the position at which the height is the lowest).

—The First Cycle—

(2) 40 mL of artificial urine (the first time) is injected from a burette with the speed of 40 mL/10 sec to the central position of the absorbent body.

(3) After 5 minutes from the start of injection of the artificial urine of the first time, approximately 60 g of filter paper with the size of 100 mm×100 mm is placed still on the liquid permeable sheet of the absorbent article with the artificial urine injection point as the center. Further, 3.5 kg of weight with the size of 100 mm×100 mm×50 mm (height) is placed still thereon. Incidentally, before being placed still on the liquid permeable sheet, the mass of the filter paper is measured.

(4) After 8 minutes from the start of injection of the artificial urine of the first time, the weight is removed, the mass of the filter paper is measured, the mass of the filter paper before the test is subtracted, and the difference is regarded as the rewetting amount (of the first time).

—The Second Cycle—

(5) After 10 minutes from the start of injection of the artificial urine of the first time, 40 mL of artificial urine (the second time) is injected from a burette with the speed of 40 mL/10 sec to the central position of the absorbent body.

(6) After 5 minutes from the start of injection of the artificial urine of the second time, approximately 60 g of filter paper with the size of 100 mm×100 mm is placed still on the liquid permeable sheet of the absorbent article with the artificial urine injection point as the center. Further, 3.5 kg of weight with the size of 100 mm×100 mm×50 mm (height) is placed still thereon. Incidentally, before being placed still on the liquid permeable sheet, the mass of the filter paper is measured.

(7) After 8 minutes from the start of injection of the artificial urine of the second time, the weight is removed, the mass of the filter paper is measured, the mass of the filter paper before the test is subtracted, and the difference is regarded as the rewetting amount (of the second time).

—The Third Cycle—

(8) The operations of (5) to (7) are repeated, and the rewetting amount (of the third time) is measured.

Incidentally, the composition of the artificial urine is as described above.

TABLE 2

| | | Example No. | | |
|---|---|---|---|---|
| | | Example 3 | Example 4 | Comparative Example 2 |
| Disposable diaper No. | | No. 4 | No. 5 | No. 6 |
| Liquid permeable sheet | Nonwoven fabric No. | No. 4 | No. 5 | No. 6 |
| | Skin side layer (the second surface) | PET/PE composite fibers | PET/PE composite fibers | PET/PE composite fibers |
| | Basis weight (g/m$^2$) | 10 | 10 | 10 |
| | Middle layer | 2 types of PET/PE composite fibers + cotton | 2 types of PET/PE composite fibers + cotton | PET/PE composite fibers |
| | Basis weight (g/m$^2$) | 9 + 1 | 9 + 1 | 10 |
| | Clothing side layer (the first surface) | 2 types of PET/PE composite fibers | 2 types of PET/PE composite fibers | 2 types of PET/PE composite fibers |
| | Basis weight (g/m$^2$) | 10 | 10 | 10 |
| | Total basis weight (g/m$^2$) | 30 | 30 | 30 |
| | Shaping processing | Not performed | Performed | Not performed |
| Rewetting amount/g | First time | 0.1 | 0.1 | 0.1 |
| | Second time | 18.9 | 18.3 | 19.3 |
| | Third time | 28.3 | 26.6 | 29.2 |

As shown in Table 2, in the disposable diapers Nos. 4 and 5, it could be understood that the rewetting amount after absorption of the artificial urine, especially at the second time (total amount of 80 mL) and at the third time (total amount of 120 mL), was lower than that compared to the disposable diaper No. 6.

Further, when the disposable diapers Nos. 4 to 6 were worn by a plurality of volunteer subjects, results were obtained in which the rewetting property is better in the disposable diapers Nos. 4 and 5 compared to the disposable diaper No. 6.

The invention claimed is:

1. A nonwoven fabric to be used for a liquid permeable sheet of an absorbent article, which includes a thickness direction, a plane direction, a first surface, and a second surface, the nonwoven fabric comprising:
    thermoplastic resin fibers; and
    cellulose based fibers a portion of which configures a plurality of separate fiber masses,
    wherein
    the nonwoven fabric comprises a plurality of gap portions which are adjacent to a first region that faces the first surface in each of the plurality of separate fiber masses,
    each of the plurality of separate fiber masses is not joined to the thermoplastic resin fibers,
    the nonwoven fabric comprises a matrix configured by the thermoplastic resin fibers and the cellulose based fibers, and
    the plurality of separate fiber masses are dispersed in the matrix.

2. The nonwoven fabric according to claim 1, wherein an outer edge in the plane direction of the plurality of gap portions is present on an outer side than an outer edge in the plane direction of the plurality of separate fiber masses.

3. The nonwoven fabric according to claim 1, further comprising a gap portion which is adjacent to a second region which faces the second surface in at least a portion of the plurality of separate fiber masses.

4. The nonwoven fabric according to claim 1, wherein the thermoplastic resin fibers are joined to each other.

5. The nonwoven fabric according to claim 1, wherein the nonwoven fabric includes the cellulose based fibers with a proportion of 3 to 35% by mass.

6. The nonwoven fabric according to claim 1, wherein the cellulose based fibers have a shorter average fiber length than the thermoplastic resin fibers.

7. The nonwoven fabric according to claim 1, wherein the cellulose based fibers include organic cotton.

8. The nonwoven fabric according to claim 1, wherein the cellulose based fibers include *Gossypium hirsutum* cotton.

9. The nonwoven fabric according to claim 1, wherein the nonwoven fabric has a multiple-layer structure which includes a skin side layer having a skin contact surface, and
the nonwoven fabric includes the plurality of separate fiber masses in a layer other than the skin side layer.

10. The nonwoven fabric according to claim 1, wherein the nonwoven fabric further comprises:
a plurality of protruded portions which protrude in a direction from the first surface to the second surface, in the second surface; and
a plurality of dented portions which are dented in a direction from the second surface to the first surface, in the first surface, wherein
each of the plurality of protruded portions and each of the plurality of dented portions are overlapped with each other in the thickness direction.

11. The nonwoven fabric according to claim 10, wherein each of the plurality of protruded portions configures a ridge portion which extends in one direction, and the nonwoven fabric further comprises a plurality of groove portions each of which is present between adjacent ridge portions and includes a groove bottom portion, wherein
each of the plurality of groove portions includes, in the groove bottom portion, a plurality of recessed portions which are disposed intermittently in the one direction and are recessed in the direction from the first surface to the second surface, each of the plurality of recessed portions including a bottom portion.

12. An absorbent article which includes a liquid permeable sheet, a liquid impermeable sheet, and an absorbent body that is present between the liquid permeable sheet and the liquid impermeable sheet, wherein
the liquid permeable sheet is the nonwoven fabric according to claim 1.

13. The absorbent article according to claim 12, wherein the second surface of the nonwoven fabric configures a skin contact surface of the liquid permeable sheet.

14. The absorbent article according to claim 12, wherein the liquid impermeable sheet has a moisture permeability.

\* \* \* \* \*